United States Patent
Lu et al.

(10) Patent No.: US 9,732,377 B2
(45) Date of Patent: Aug. 15, 2017

(54) MICROFLUIDIC SYSTEMS AND METHODS FOR CHROMATIN IMMUNOPRECIPITATION (CHIP)

(71) Applicants: Chang Lu, Blacksburg, VA (US); Zhenning Cao, Blacksburg, VA (US)

(72) Inventors: Chang Lu, Blacksburg, VA (US); Zhenning Cao, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 61 days.

(21) Appl. No.: 14/511,422

(22) Filed: Oct. 10, 2014

(65) Prior Publication Data

US 2015/0105287 A1 Apr. 16, 2015

Related U.S. Application Data

(60) Provisional application No. 61/889,725, filed on Oct. 11, 2013.

(51) Int. Cl.
*B01L 3/00* (2006.01)
*C12Q 1/68* (2006.01)
(Continued)

(52) U.S. Cl.
CPC ...... *C12Q 1/6806* (2013.01); *B01L 3/502761* (2013.01); *G01N 33/54326* (2013.01); *G01N 33/6875* (2013.01); *B01L 2200/0668* (2013.01); *B01L 2300/0816* (2013.01); *B01L 2300/0877* (2013.01); *B01L 2400/043* (2013.01); *B01L 2400/0487* (2013.01); *C12Q 2522/10* (2013.01); *C12Q 2565/629* (2013.01)

(58) Field of Classification Search
None
See application file for complete search history.

(56) References Cited

U.S. PATENT DOCUMENTS

2006/0275179 A1* 12/2006 Viovy ................. B01F 13/0059
422/400

OTHER PUBLICATIONS

Geng et al., Histone modification analysis by chromatin immunoprecipitation from a low number of cells on a microfluidic platform, Lab on a Chip, 11, pp. 2842-2848, published online Jul. 13, 2011.*

(Continued)

*Primary Examiner* — Rebecca Martinez
(74) *Attorney, Agent, or Firm* — Whitham, Curtis & Cook, P.C.

(57) ABSTRACT

An integrated microfluidic chromatin immunoprecipitation assay dramatically improves the collection efficiency of ChIP DNA from cells. Immunoprecipitation of chromatin fragments is conducted in a microfluidic chamber with a large fraction of its volume (e.g., ~15-40%) occupied by magnetic immunoprecipitation (IP) beads. Oscillating washing of the beads, enabled by, e.g., solenoid valves (controlled by a computer) and high pressure attached to both ends of the microfluidic chamber, effectively removes unbound chromatin and produces high-quality ChIP DNA. ChIP DNA produced by an example device generates excellent results in the subsequent DNA library preparation. The ChIP-seq (i.e., ChIP followed by next-generation sequencing) results match very well with public data generated using much larger cell sample sizes and a conventional approach.

16 Claims, 20 Drawing Sheets

(51) Int. Cl.
*G01N 33/543* (2006.01)
*G01N 33/68* (2006.01)

(56) References Cited

OTHER PUBLICATIONS

Geng, T., et al., "Genomic DNA Extraction from Cells by Electroporation on an Integrated Microfluidic Platform", Anal. Chem. 84, pp. 9632-9639 (2012).

* cited by examiner

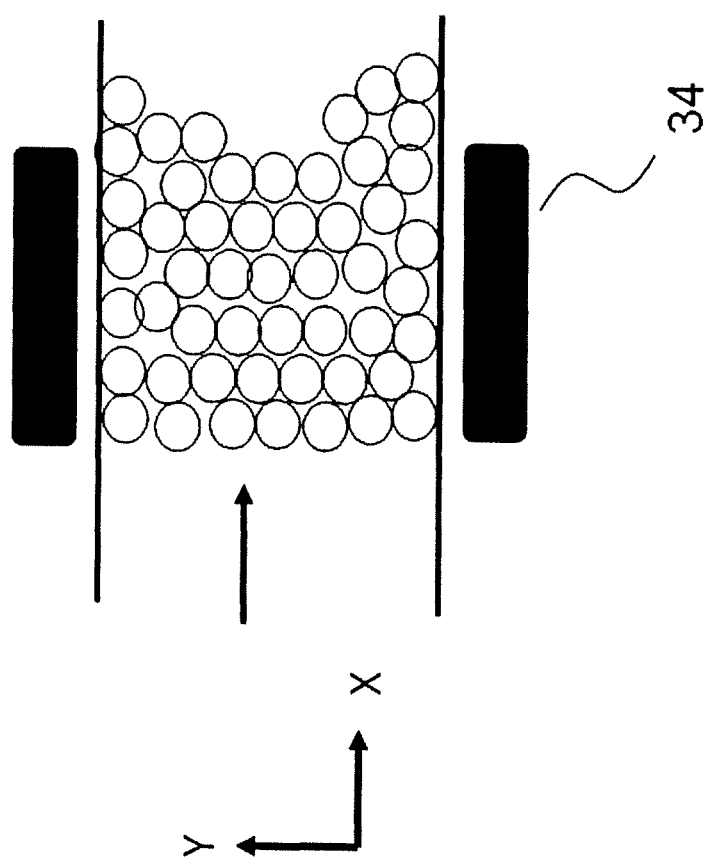

```
                         SEQUENCE LISTING

<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 1
aggataatca gcccctgaat a                                                   21

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 2
tccatcagtc agtccgcagt                                                     20

<210> SEQ ID NO 3
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 3
cagccaccca cctaggaa                                                       18

<210> SEQ ID NO 4
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 4
tcctatggct ccccaggt                                                       18

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide primer
```

<400> SEQUENCE: 5
tcatctgcaa atggggacaa                                       20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 6
aggacacccc ctctcaacac                                       20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 7
atggttgcca ctggggatct                                       20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 8
tgccaaagcc taggggaaga                                       20

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 9
cagcacctcc agcccttat                                        19

<210> SEQ ID NO 10
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 10
tccccagagg gaggaaag                                         18

<210> SEQ ID NO 11
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 11
ctcggccttg atcttctcc                                        19

<210> SEQ ID NO 12
<211> LENGTH: 20

-continued

```
<212> TYPE: DNA
<213> ORGANISM: Artificial Sequence
<220> FEATURE:
<223> OTHER INFORMATION: Synthetic oligonucleotide primer

<400> SEQUENCE: 12
tctggctttc ttcgcttttc                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 13
cgtcttcgta tgccatcaac                                              20

<210> SEQ ID NO 14
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 14
gttgaacacg ggtcagtcg                                               19
```

MICROFLUIDIC SYSTEMS AND METHODS FOR CHROMATIN IMMUNOPRECIPITATION (CHIP)

CROSS-REFERENCE TO RELATED APPLICATIONS

This application claims benefit of U.S. provisional patent application No. 61/889,725 filed Oct. 11, 2013, the complete contents of which are herein incorporated by reference.

STATEMENT OF FEDERALLY SPONSORED RESEARCH AND DEVELOPMENT

This invention was made with government support under contract CBET-1016547 awarded by the National Science Foundation. The government has certain rights in the invention.

SEQUENCE LISTING

This application includes as the Sequence Listing the complete contents of the accompanying text file "Sequence.txt", created Oct. 8, 2014, containing 3.07 kilobytes, hereby incorporated by reference.

FIELD OF THE INVENTION

The present invention relates generally to microfluidic analysis systems, and in particular, to the use of magnetic beads for chromatin immunoprecipitation.

BACKGROUND

The interactions between protein and DNA are critically involved in a wide range of biological processes and disease conditions including cancer. Chromatin immunoprecipitation (ChIP) assay has become the technique of choice for examining in vivo DNA-protein interactions over the years. In a typical ChIP experiment, the DNA-binding protein (e.g. a transcription factor or a histone) is crosslinked to DNA in vivo by treating cells with formaldehyde. The cells are then lysed in order to release chromosomes and the chromatin is sheared by sonication into small fragments of 200-600 bp in the size. DNA fragments associated with the protein are then enriched by immunoprecipitation (e.g., using immunoprecipitation (IP) beads coated by an antibody specific to the transcription factor or histone). Finally, the crosslinks are reversed and the released DNA is assayed to determine the sequences bound by the protein. The identification of the DNA sequences can be done by qPCR if there are known candidate promoters. Alternatively, these binding sites can be mapped at the genome scale by hybridization into a microarray (ChIP-chip) or by sequencing (ChIP-seq) using high-throughput sequencing technology (e.g. Illumina genome analyzer). In general, ChIP-seq has higher resolution, fewer artifacts, greater coverage and a larger dynamic range than ChIP-chip and provides data of improved quality.

Although current ChIP-related assays have been generating useful data, the technique has some serious limitations. First, a key limitation is the requirement for a large number of cells (>$10^6$ cells per IP for ChIP-qPCR and $10^7$-$10^8$ cells for ChIP-seq). This is usually feasible with cell lines but poses a serious challenge when primary cells are used. The sample amount generated by lab animals and patients is very limited. For example, the number of naturally occurring T regulatory cells in murine splenocytes is ~10,000 per spleen, and ~5000 per ml peripheral blood leukocyte. Circulating tumor cells are present by the frequency of 1-10 per ml of whole blood in patients with metastatic cancer. In addition, primary samples typically contain a mixture of different cell types. The enrichment and isolation of a homogenous single cell type not only add time and labor to the protocol but also generate further loss in the sample amount. Second, most ChIP assays involve extensive manual handling and take 3-4 days or longer to finish. These cumbersome procedures may create loss of materials and technical errors that lead to inconsistencies between replicates. There have been modifications and improvements made to ChIP protocols to make the assays shorter and easier and more importantly, allow use of small cell populations (e.g. ~100-1000 cells for ChIP-qPCR, and ~10,000 cells, involving whole genome amplification, for ChIP-seq). However, most of these improved protocols still involve a significant amount of manual processing.

Standard next-generation sequencing protocols require a sufficient amount of DNA (~5 ng). Thus high efficiency extraction of ChIP DNA from cells often represents a critical roadblock for sensitive ChIP assays. Recent studies by Bernstein and his co-workers developed Nano-ChIP-seq procedure for performing ChIP-seq assays with limited samples. Although they achieved successful DNA sequencing from as few as 10,000 cells, only about 10~50 pg of DNA is pulled down during the immunoprecipitation step. With this tiny amount of DNA, extensive amplification steps were required to generate enough material for library preparation and sequencing. However, pre-amplification also tends to introduce artifacts and biases and leads to low-quality results from DNA sequencing.

SUMMARY

Exemplary embodiments of the present invention simultaneously address two problems which plague known ChIP techniques. The first problem is collecting enough DNA by immunoprecipitation to permit subsequent assay steps such as sequencing. The second problem is obtaining high quality immunoprecipitated DNA with high enrichment. In addition to binding intended antigens, IP beads also exhibit non-specific binding with "junk" chromatin that undesirably contributes to a fraction of the recovered DNA that goes on to further processing in the assay. Limitations of existing ChIP techniques are overcome by a highly efficient microfluidic ChIP system and method for extracting ChIP DNA. Exemplary embodiments employing microfluidic ChIP technology as described herein provide superior immunoprecipitation over existing art for several reasons. First, microfluidic chambers offer tiny volumes that build up high concentrations from trace amounts of molecules. Such high concentrations facilitate adsorption kinetics and completeness. Second, in some exemplary embodiments, IP beads take up a substantial fraction of the tiny volume of the microfluidic chamber (e.g. 15-40%, compared to 5% in the standard ChIP[28]) so that the surface area/volume ratio is large. The increased contact between the bead surfaces (coated with antibody) and the target protein-DNA complexes promotes high efficiency for ChIP. Third, a unique feature of exemplary embodiments is structures and setup for oscillatory washing of the IP beads. As detailed below, alternating pressure pulses are applied at the two ends of the microfluidic chamber to move the beads back and forth. Such arrangement effectively removes nonspecific adsorption after high efficiency adsorption. Finally, microfluidics also offers the additional benefits of integrating various steps of a chromatin immunoprecipitation assay and minimizing material losses among these steps.

Taking advantage of the improvement in immunoprecipitation efficiency in a microscale chamber, the duration of immunoprecipitation is shortened from overnight (in conventional protocols) to less than 100 min in exemplary embodiments. After optimizing the bead coating and bead amount, >1 ng ChIP DNA was successfully extracted from as few as 10000 cells. This yield was roughly ~100 fold higher than that of previous reports (10~50 pg from 10000 cells)[22, 25]. As an example, the microfluidic ChIP technology was used to examine the tri-methylation of lysine 4 and 27 of histone 3 in GM12878 cells (a lymphoblastic cell line) at the genome level.

BRIEF DESCRIPTION OF THE DRAWINGS

FIG. 2A shows magnetic immunoprecipitation (IP) beads loaded into a microfluidic chamber and packed against the partially-open microfluidic valve. FIG. 2B-2C show chromatin solution being loaded and flowed through the packed bead bed.

FIG. 4A shows the solution containing unbound chromatin flow into the outlet, while the magnetic beads are retained inside the microfluidic chamber by an external magnet. FIG. 4B shows the magnetic beads being transferred from the microfluidic chip into an Eppendorf tube for further analysis.

FIG. 5A-5D shows four (4) separate diagrammatic illustrations of alternative microfluidic structures for bead trapping while allowing flow of solution. FIGS. 5A and 5B show, respectively, an embodiment having a decrease in the channel height or in the channel width at the exit of the chamber. FIG. 5C shows the use of magnets to apply a magnetic field in the z direction (vertical to the XY plane). FIG. 5D shows the application of a magnetic field within the XY plane.

FIG. 7A shows data on Lys4 trimethylation (H3K4me3). (FP and SP) are the positive loci and (SN and Set1) are the negative loci. FIG. 7B shows data on Lys27 trimethylation (H3K27me3). NODAL and PAX6 are positive loci and Set1 is the negative locus. These qPCR tests were done with ChIP DNA samples each extracted from 10000 cells.

FIG. 11A shows H3K4me3 examined using 1000 cell sample. FIG. 11B shows H3K27me3 examined using 10000 cells.

FIG. 13A shows data on Lys4 trimethylation (H3K4me3). FIG. 13B shows data on Lys27 trimethylation (H3K27me3).

DETAILED DESCRIPTION

As used generally in the art, "immunoprecipitation" (IP) is the process of precipitating a protein antigen out of a solution using an antibody that specifically binds the target antigen. "Chromatin immunoprecipitation" (ChIP), as was discussed in the Background section above, involves using antibodies to target proteins of chromatin (e.g., histones and transcription factors). This permits DNA fragments associated with the proteins to be enriched. One approach to ChIP is the use of immunoprecipitation (IP) beads coated with a specific antibody. As used herein, immunoprecipitation is regarded as complete when IP beads are subject to no additional processing prior to recovery step(s) which remove the crosslinks binding the DNA with the proteins which are bound to the IP beads.

Figure 1A:
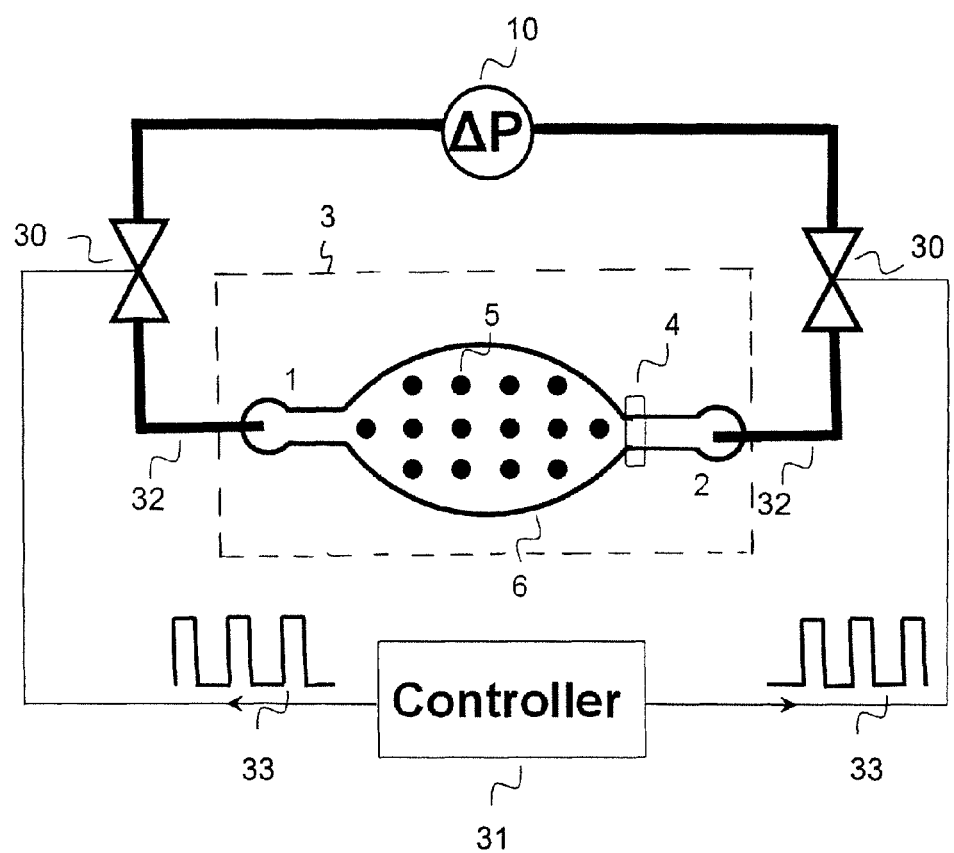
FIGS. 1A and 1B show schematics of exemplary systems for microfluidic chromatin immunoprecipitation (ChIP).

Referring now to the drawings, FIG. 1A shows a schematic of an exemplary microfluidic chromatin immunoprecipitation (ChIP) system which includes one or more of a microfluidic chip 3, tubing 32 (e.g., Teflon or PFA tubing), one or more solenoid valves 30, pressure source 10 (e.g., an air pressure source), and controller 31 for controlling actuation of solenoid valves 30. The microfluidic chip 3 comprises at least one microfluidic chamber 6 which is connected to an inlet 1 (e.g., an inlet channel) and an outlet 2

(e.g., an outlet channel) at its two ends. Micropillars 5 are positioned inside the microfluidic chamber 6 to support the chamber and avoid collapse. The structures 1, 2, 5, and 6 are in the fluidic layer of the microfluidic chip 3. An on-chip valve 4 is a channel in the control layer of the microfluidic chip 3 and functions as a micromechanical valve when it is pressurized. The fluidic layer and control layer are stacked, separated by a thin membrane. The on-chip valve 4 arranged at/above the outlet 2 allows partial or restricted closure of the fluidic layer to stop magnetic immunoprecipitation (IP) beads while allowing flow of liquid through outlet 2. In an alternative embodiment, an additional on-chip valve 4 may be arranged at/above the inlet 1.

Figure 1B:
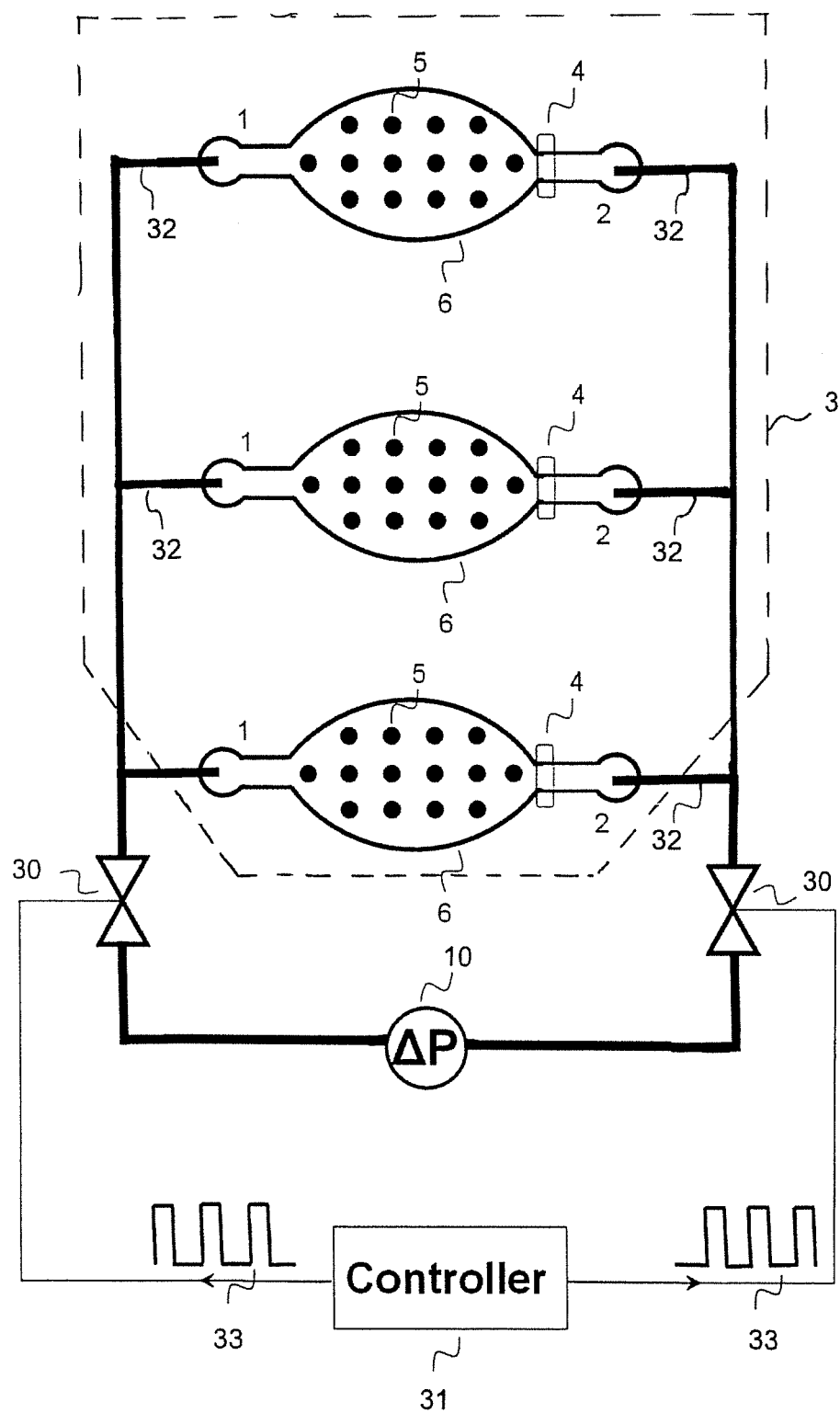

In some aspects, the invention provides an apparatus comprising multiple microfluidic chambers 6 (e.g. an array of microfluidic chambers) as described herein, e.g., for high throughput treatment of multiple chromatin samples at the same time. FIG. 1B shows a system schematic with multiple parallel microfluidic chambers 6 included in the apparatus on the same microfluidic chip 3. In some aspects, the multiple microfluidic chambers are placed in parallel, e.g. side-by-side, and in other aspects, they are stacked in the apparatus. The plurality of devices may be served by either individual or common sources of chromatin-containing fluid, washing buffer, etc., and/or selected microfluidic chambers may be grouped together and connected to a common source while others are grouped and served by another source. In this manner, the type of chromatin, or the conditions under which the chromatin is provided, may be varied as desired, as may the composition of the washing buffer, e.g., to accommodate or test different antibody binding affinities for different samples.

The terms "outlet" and "inlet" are used herein for clarity in distinguishing that a microfluidic chamber 6 generally has at least two separate ends/openings. However, these terms do not necessarily limit the functional capability or use of either end of the microfluidic chamber 6, and either or both the inlet 1 and the outlet 2 may be used for allowing objects (e.g., IP beads) or liquids (e.g., chromatin-containing fluid) to enter or exit the microfluidic chamber 6 if so desired for a particular embodiment.

Various methods and parameters for fabrication of a microfluidic chip 3 or a microchamber 6 will be apparent to one of skill in the art. As just one illustrative example, the microfluidic chip 3 may be advantageously fabricated out of polydimethylsiloxane (PDMS) using multilayer soft lithography techniques as described in previous publications[29, 30] Briefly, two photomasks were first generated with microscale patterns designed with computer-aided design software FreeHand MX (Macromedia, San Francisco, Calif., USA) and printed on high-resolution (5,080 dpi) transparencies. The master for the control layer (~50 in the photoresist thickness) and the fluidic layer (~40 μm thick photoresist) were made of negative photoresist SU-8 2025 (Microchem, Newton, Mass., USA) spun on a 3-inch silicon wafer (University Wafer, South Boston, Mass., USA). Afterwards, PDMS at a mass ratio of RTV615 A:RTV615 B=20:1 was poured onto the fluidic layer master in a Petri dish to generate ~5 mm thick fluidic layer. PDMS at a mass ratio of RTV615 A:RTV615 B=5:1 was spun onto the control layer master at 1100 rpm for 35 s, resulting in the thin control layer (~108 μm in the thickness of the PDMS). Both layers of PDMS were partially cured at 80° C. for 30 min. The fluidic layer was then peeled off from the master after cutting by a razor blade. The control layer stamp was aligned with and bonded to the fluidic layer. The two-layer PDMS structure was baked at 80° C. for another 60 min, peeled off from the flow layer master, and punched to produce inlet and outlet reservoirs. Once the two-layer PDMS and a pre-cleaned glass slide were treated with oxygen plasma, it was immediately brought into contact against the slide to form closed channels. Finally, the assembled chip was baked at 80° C. for another 1 h to promote the bonding strength between PDMS and glass. Glass slides were cleaned in a basic solution ($H_2O$:27% $NH_4OH$:30% $H_2O_2$=5:1:1, volumetric ratio) at 75° C. for 2 h and then rinsed with ultrapure water and thoroughly blown dry. This example fabrication process is not intended to be limiting. Alternative steps and/or parameters for the manufacture of microfluidic chips and microfluidic chambers may be employed in the practice of the invention.

FIGS. 2A-2C, 3A-3D, and 4A-4B schematically illustrate an exemplary microfluidic ChIP procedure. Generally, an exemplary method may comprise steps of loading a microfluidic chamber with a plurality of magnetic immunoprecipitation (IP) beads; packing the plurality of magnetic IP beads into a bed; passing a chromatin-containing fluid through the bed so as to permit adsorption of chromatin to surfaces of the magnetic IP beads; and alternately applying pressure pulses so as to oscillate one or more of said plurality of magnetic IP beads and said chromatin-containing fluid between an inlet and an outlet of the microfluidic chamber. After the oscillating washing step, the IP beads are retained in the microfluidic chamber while the microfluidic chamber is flushed by a buffer. Finally the IP beads are collected and the chromatin recovered therefrom for completion of a full ChIP assay.

Generally, a microfluidic chamber 6 needs to be prepped prior to admittance of IP beads and chromatin-containing solution. As one example, the microfluidic chamber 6 is initially rinsed with PBS with 0.02% Tween 20 (Sigma-Aldrich) to condition the channel and remove impurities.

Subsequently, the IP beads 7 are loaded into the microfluidic chamber 6. This may be accomplished using, for example, the combined effects of pump-driven pressure and magnetic force generated by an external magnet (e.g., NdFeB permanent magnet (K&J Magnetics, Jamison, Pa., USA)). In exemplary embodiments, the IP beads 7 are antibody coated/functionalized superparamagnetic beads. The amount of IP beads 7 admitted to microfluidic chamber 6 is preferably such that the beads fill 15-40% of the volume of the microfluidic chamber 6.

The microfluidic on-chip valve 4 is partially closed so as to permit the passage of liquid or solution but prevent passage of the IP beads 7. This allows the IP beads 7 to be packed against the valve 4 to form a packed bed as shown FIG. 2A.

Figure 2A:
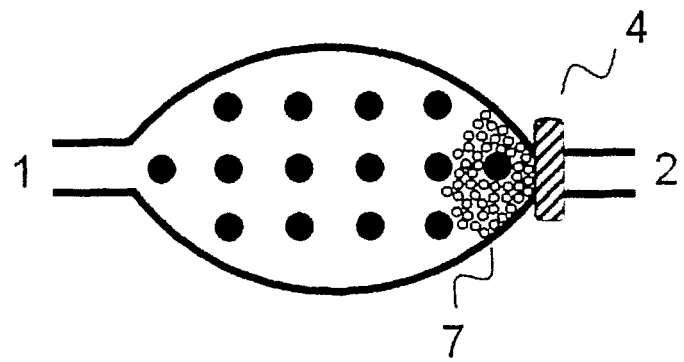
FIG. 2A-2C show three (3) separate diagrammatic illustrations of the operational procedures for microfluidic ChIP.
Figure 2B:
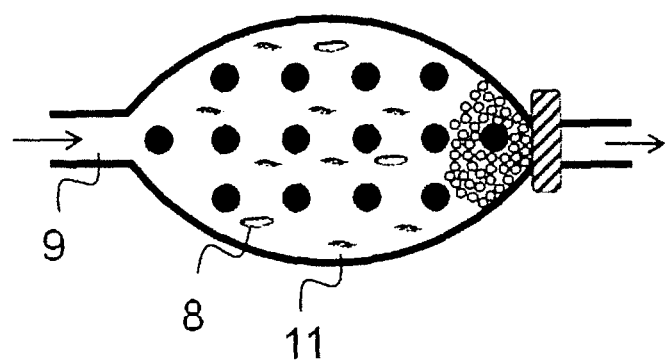
Figure 2C:
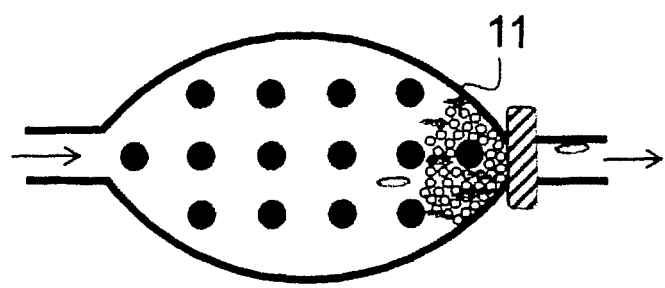

After the loading of the IP beads 7, a volume of solution 9 (e.g., approx. 50-100 μl) containing chromatin fragments is passed through the packed bed of IP beads 7. This permits the chromatin fragments 11 containing the protein targeted by the antibody coating the IP beads 7 to adsorb efficiently on the surfaces of the beads (FIGS. 2B and 2C). The untargeted chromatin 8 and other cellular debris may flow out the chamber as depicted in FIG. 2C.

As discussed above, a problem with known applications of IP beads is a difficulty in obtaining high quality DNA from the immunoprecipitation with as little non-specifically bound DNA as possible. While the large volume percentage of IP beads 7 in the microfluidic chamber 6 helps address the problem of collecting a sufficient amount of DNA, it is alone generally inadequate for routinely providing high quality DNA as measured by, for example, relative fold enrichment. Exemplary embodiments of the present invention address the problem of the DNA quality per a step of oscillating washing of the IP beads after initial adsorption.

Figure 3A:
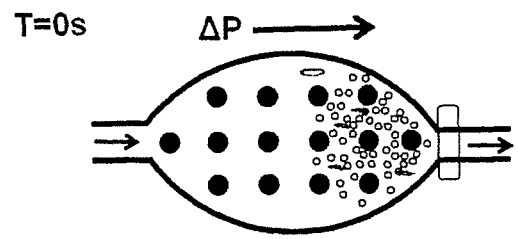
FIG. 3A-3D show four (4) time lapse diagrammatic illustrations of the process of microfluidic oscillatory washing.
Figure 3B:
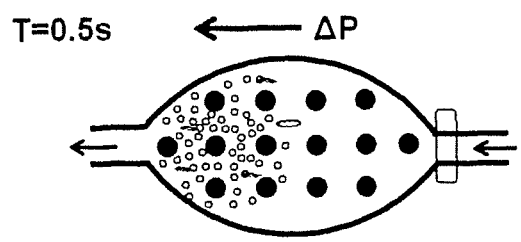
Figure 3C:
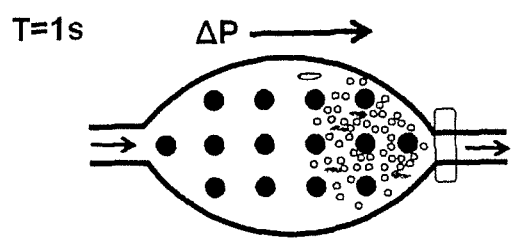
Figure 3D:
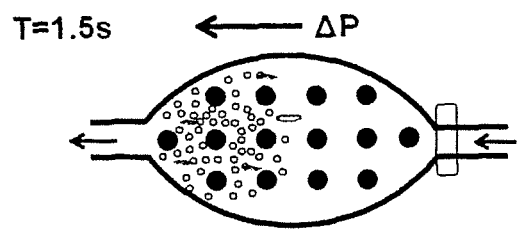

After passing the chromatin-containing solution 9 through the IP beads 7 such that the chromatin fragments 9 bind to the antibody-coated surfaces thereof, a washing buffer is introduced into the microfluidic chamber 6 and the packed IP beads 7 are resuspended inside the chamber 6. The tubing 32 is prefilled with washing buffer (e.g., 10 μl) at each end of the microfluidic chamber 6 and the on-chip valve 4 is kept partially-open (whereby IP beads 7 cannot pass) or fully open. In either case, washing buffer is permitted to pass. In one exemplary implementation of the oscillating washing, alternating pressure pulses ΔP are applied at either end of the microfluidic chamber through the tubing 32. The pressure pulse parameters such as duration and frequency are regulated by operation of one or more solenoid valves 30 connected in between the pressure source 10 (e.g., a gas cylinder) and the ends of the microfluidic chamber 6, as shown in FIG. 1A. The solenoid valves are controlled and actuated by a controller 31 which may be a computer which outputs control signals 33 using a DAQ card (e.g., NI SCB-68; National Instruments, Austin, Tex., USA) and programmed computer instructions implemented on, e.g., a LabVIEW (National Instruments) program. Exemplary pressure pulse parameters include pulse durations of 0.1-0.5 s inclusive and/or frequency of the pressure pulses between 2 and 10 Hz, such range being inclusive of 2 and 10 Hz. The pressure provided by the pressure source 10 may be, for example, 1.5 psi or under, between 1.5 and 1 psi, between 1 psi and 0.5 psi, or under 0.5 psi. The pressure source 10, like the solenoid valves 30, may be controlled by the controller 31 to set, adjust, or vary the pressure amount or profile of each pressure pulse ΔP. The frequency and duration of these pressure pulses ΔP can vary depending on the implementation, with factors for their determination including one or more of i) the dimensions of the microfluidic chamber 6 for a given embodiment, ii) the intensity of the pressure, and iii) the amount of IP beads inside the chamber. During the oscillatory washing process, it is preferable that the IP beads 7 stay inside the microfluidic chamber 6 without being washed out of the inlet 1 or outlet 2. A typical oscillatory washing process is shown in FIG. 3A-3D. The first pulse (applied in this example at the left end of the microfluidic chamber, as shown in FIG. 3A) pushes the IP beads 7 (together with adsorbed molecules) toward the right end inside the chamber. After the first pulse, the second pulse is applied at the right end of the microfluidic chamber and pushes the beads toward the left side inside the chamber (FIG. 3B). Such cycles are then repeated for a plurality of iterations (FIGS. 3C and 3D). The intensity, frequency, and duration of the pressure pulses ΔP may be varied to optimize the washing efficiency for different embodiments. The pressure pulses 10 generally move both the washing buffer in which the beads are suspended as well as the IP beads. Not to be bound by theory, one acceptable manner of describing the motion of these elements is as follows: the rapid switch in direction of the applied pressure pulses ΔP causes a substantially instantaneous change in fluid flow direction (e.g., to the left or to the right as depicted in FIG. 3A-3D). In the immediate aftermath of each change in fluid flow direction, the inertia of the IP beads 7 causes a small delay in their change in direction. As a result, with each new pressure pulse the fluid and IP beads temporarily move in opposing directions, facilitating the washing of the IP beads 7. The oscillating washing process has the benefit of dislodging and removing chromatin that is non-specifically bound to the antibody-coating of the IP beads 7, resulting in substantially improved relative fold enrichment.

In an alternative embodiment, an individual solenoid valve 30 may be used which is configured, together with the pressure source 10, to provide both positive and negative pressure pulses at one end (e.g., inlet 1 or outlet 2) of the microfluidic chamber 6. As yet another alternative, a directional control valve may be used and configured so as to repetitively switch the application of pressure from the pressure source 10 between the inlet 1 and outlet 2.

Figure 4A:
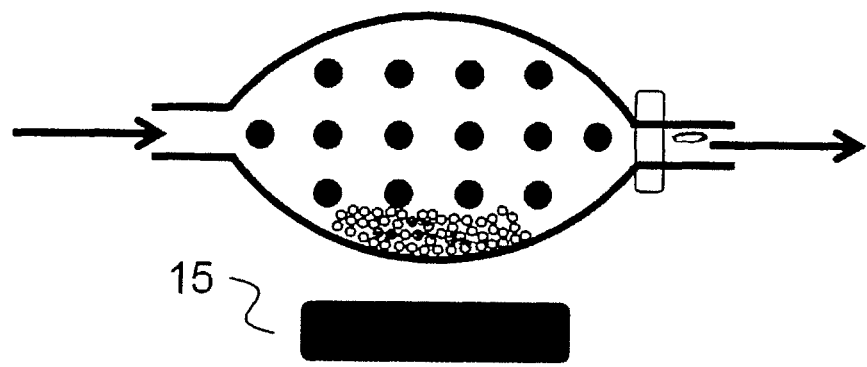
FIGS. 4A and 4B show two (2) separate diagrammatic illustrations of a procedure of collecting magnetic beads from a microfluidic chip.
Figure 4B:
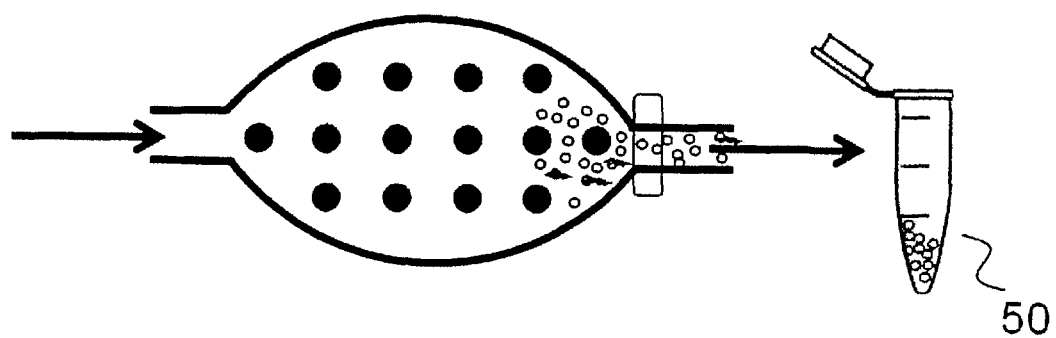

After the oscillatory washing, the IP beads 7 are separated from the washing fluid containing unbound chromatin fragments and other debris. According to one exemplary embodiment as shown in FIG. 4A, the IP beads 7 are retained by a magnet 15 (e.g., a NdFeB magnet) to one side of the microfluidic chamber 6 while the unbound chromatin fragments 8 and other debris/waste are flushed out of the microfluidic chamber 6 by a buffer (e.g., neat buffer). The oscillatory washing process and the flushing step in FIG. 4A may be repeated several times until satisfactory washing results are achieved. Finally, the IP beads 7 are flowed out of the microfluidic chamber 6 under an appropriate flow rate and collected. For example, the IP beads 7 may be collected into a low binding Eppendorf tube 50 containing TE buffer (FIG. 4B). The IP beads 7 (with bound chromatin fragments) are ready for further processing and DNA analysis (e.g., by qPCR or sequencing).

Figure 5A:
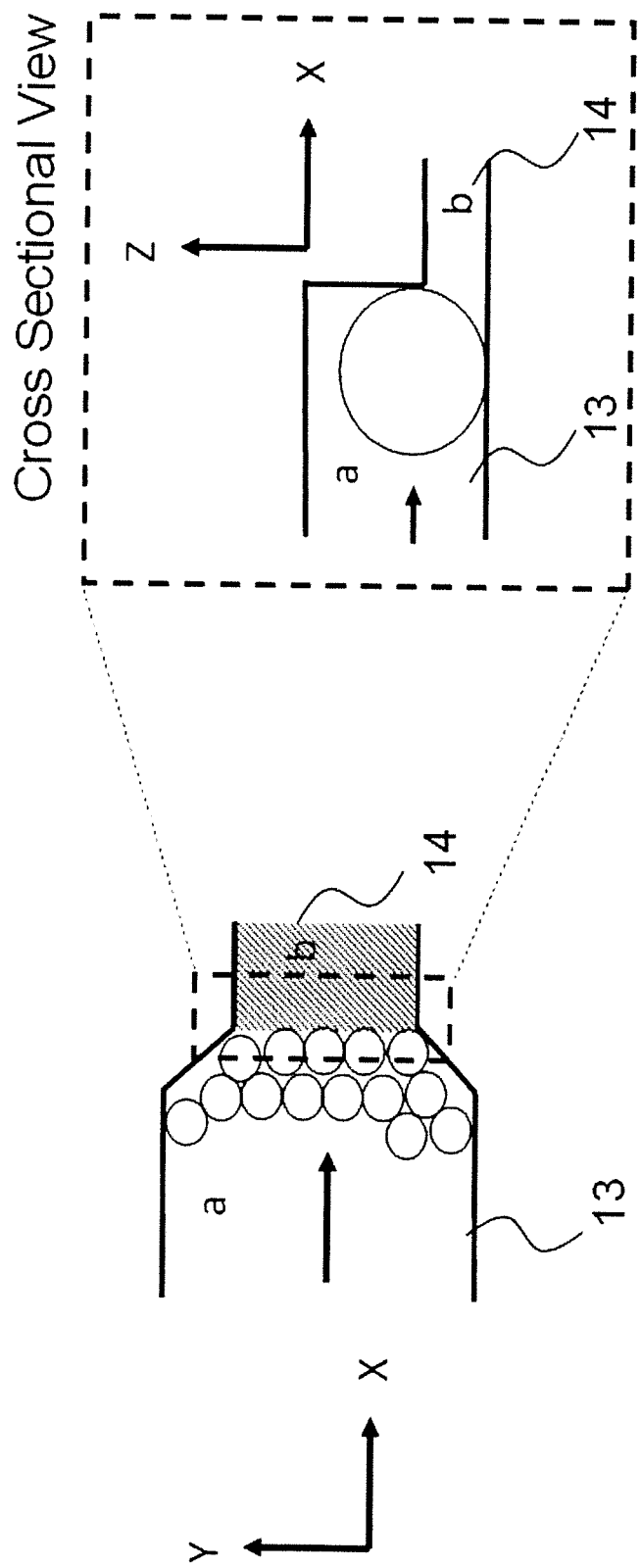
Figure 5B:
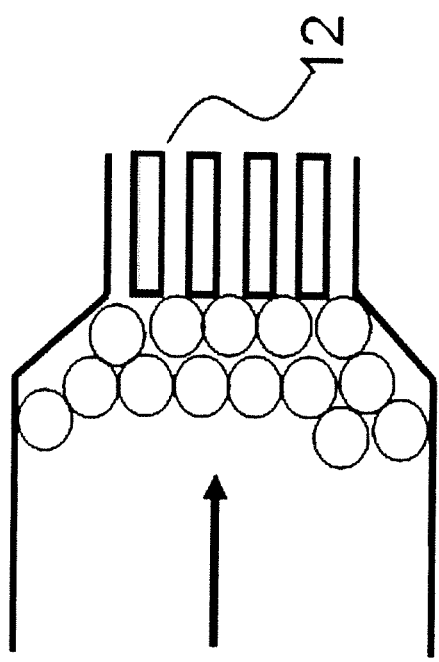
Figure 5C:
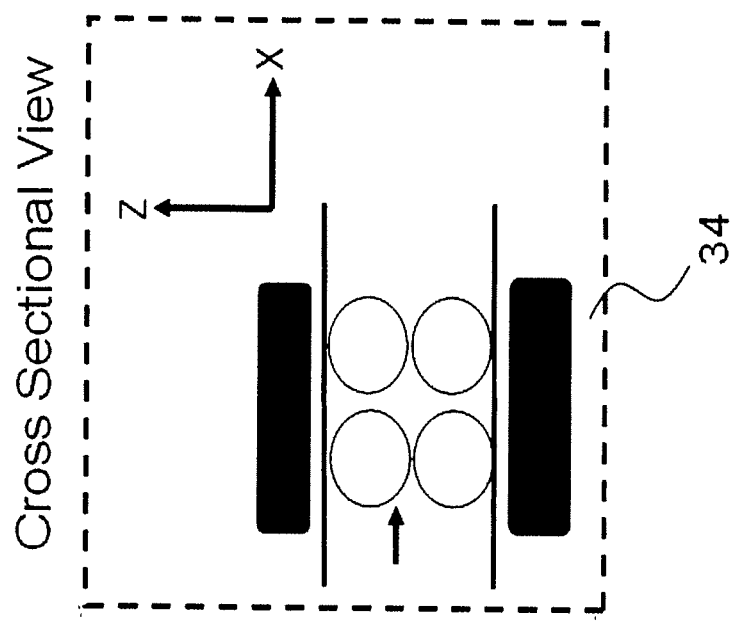
Figure 5C:
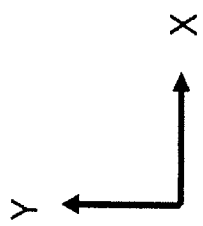

FIG. 5A-5D show alternative implementations for on-chip valve 4. As a non-exhaustive list of alternatives, four alternative microfluidic structures or setups may also be used to trap IP beads while allowing liquid flow. As shown in FIG. 5A, IP beads may be trapped due to a decreased channel depth from channel (a) 13 to channel (b) 14. Alternatively, as shown in FIG. 5B, beads can be trapped as a result of having structures and channels with dimensions smaller than that of the beads (e.g. a pillar array 12). Magnet(s) can also be applied to trap magnetic beads inside a microfluidic channel while allowing liquid flow, as shown in FIGS. 5C and 5D. In FIG. 5C, the two magnets 34, with opposite poles facing each other, are placed on the top and bottom of the microfluidic channel. In FIG. 5D, the two magnets 34, with opposite poles facing each other, are placed on the left and right side of the microfluidic channel.

The microfluidic systems and methods of this invention may be used for ChIP assay of a wide range of cells with potential scientific interest. Exemplary cell types include but are not limited to: cells from primary culture; cells from established cell lines; cells from biological samples such as blood or tissue samples, etc. The cells may be prokaryotic or eukaryotic, and may be from an animal or plant source.

To describe the present invention by way of examples, the inventors conducted a series of experiments, which are described below. These examples are provided for illustrative purpose only, and should not be considered as limiting the invention.

EXAMPLE

A microfluidic design of the type shown in FIG. 1 has been tested using sonicated chromatin of GM 12878 cell line. GM12878 cells were from ATCC and propagated in RPMI 1640 (Invitrogen) plus 15% fetal bovine serum, 100 U penicillin-100 mg streptomycin/ml (Invitrogen) at 37° C. in a humidified incubator containing 5% $CO_2$. Cells were subcultured every two days to maintain them in exponential growth phase. Once harvested, the cells were centrifuged at 1,600×g for 5 min at room temperature in a swing bucket centrifuge with soft deceleration. The cells were washed twice with 1.0 ml room temperature 1×PBS each time by centrifugation and resuspension. Cells were cross-linked for 5~10 mM with 1 ml 1% freshly-made formaldehyde and the crosslinking was then terminated by adding 0.05 ml 2.5M glycine (final concentration is 0.125 M) and shaking for 5 min at room temperature. The crosslinked cells were pelleted and washed with pre-cooled PBS buffer and resuspended in the sonication buffer (Covaris, 10 mM Tris-HCl, pH8.1, 1 mM EDTA, 0.1% SDS, 1 mM PMSF (Sigma-Aldrich) and 1% protease inhibitor cocktail (Sigma-Aldrich), Note: the PMSF and protease inhibitor cocktail should be added freshly) by vortexing. The cell samples were sonicated with Covaris S2 sonicator in the Covaris snap cap glass sonication tube for 14 min with 5% duty, level 3 intensity and 200 burst. The sonicated lysate was centrifuged at a speed of 14000×g for 10 min under 4° C. The pre-cleared chromatin (22 or 120 µl, containing chromatin from 10000 cells per 120 µl) in the supernatant was transferred to a new low-bind Eppendorf tube for subsequent microfluidic ChIP in accordance with an exemplary embodiment of the present invention. 45% (with 22 µl total sample amount) or 17% (with 120 µl total sample amount) of the chromatin sample was taken out and measured as input for admitting to the microfluidic chamber 6. Solution 9 containing fragmented chromatin was snap frozen and stored before use at −80° C. in single use aliquots (20 µl for each) to avoid repeated freeze/thaw cycles. FIG. 2B shows introduction of chromatin-containing solution 9 to the microfluidic chamber 6.

Superparamagnetic Dynabeads® Protein A (2.8 µm, 30 mg/ml; Invitrogen, Carlsbad, Calif., USA) were used for manufacturing the immunoprecipitation (IP) beads. The beads were washed twice with freshly prepared and ice-cold blocking buffer [1× phosphate buffered saline (PBS; Sigma-Aldrich, St. Louis, Mo., USA) containing 5 mg/ml bovine serum albumin (BSA; Sigma-Aldrich)] and resuspended in the blocking buffer. The blocked beads were gently mixed with the antibody [anti-trimethyl-Histone H3 (Lys4) antibody, or anti-trimethyl-Histone H3 (Lys27) antibody; Millipore, Billerica, Mass., USA)], and incubated at 4° C. overnight on a rotator with a low speed. The prepared IP beads 7 with antibody-coating were then washed twice with the blocking buffer and resuspended in the buffer to perform microfluidic ChIP assays.

To set up the ChIP system (FIG. 1A), the reagents were introduced into the inlet 1 via perfluoroalkoxyalkane (PFA) high purity tubing (1622L; IDEX Health &Science LLC, Oak Harbor, Wash., USA) with the flow driven by a syringe pump (Fusion 400; Chemyx, Stafford, Tex., USA). The on-chip microfluidic valve 4 was actuated by a solenoid valve (ASCO Scientific, Florham Park, N.J., USA) and a pressure source 10. A DAQ card (NI SCB-68; National Instruments, Austin, Tex., USA) and a LabVIEW (National Instruments) program were employed to control the switching of the solenoid valve. The applied pressure in the PDMS control channel deforms the thin PDMS membrane (~95 µm in thickness) between the fluidic and control channels and closes the fluidic channel partially (due to the square cross section of the fluidic channel) to stop IP beads while allowing liquid flow[29]. A pressure regulator was used to adjust the pressure from pressure source 10, and the working pressure was typically between 35 and 40 psi. Prior to experiments, the control channels were pre-filled with water to prevent bubble formation in fluidic channels. Microfluidic ChIP assay was monitored by a CCD camera (ORCA-285, Hamamatsu, Bridgewater, N.J., USA) mounted on the port of an inverted microscope.

Figure 6:
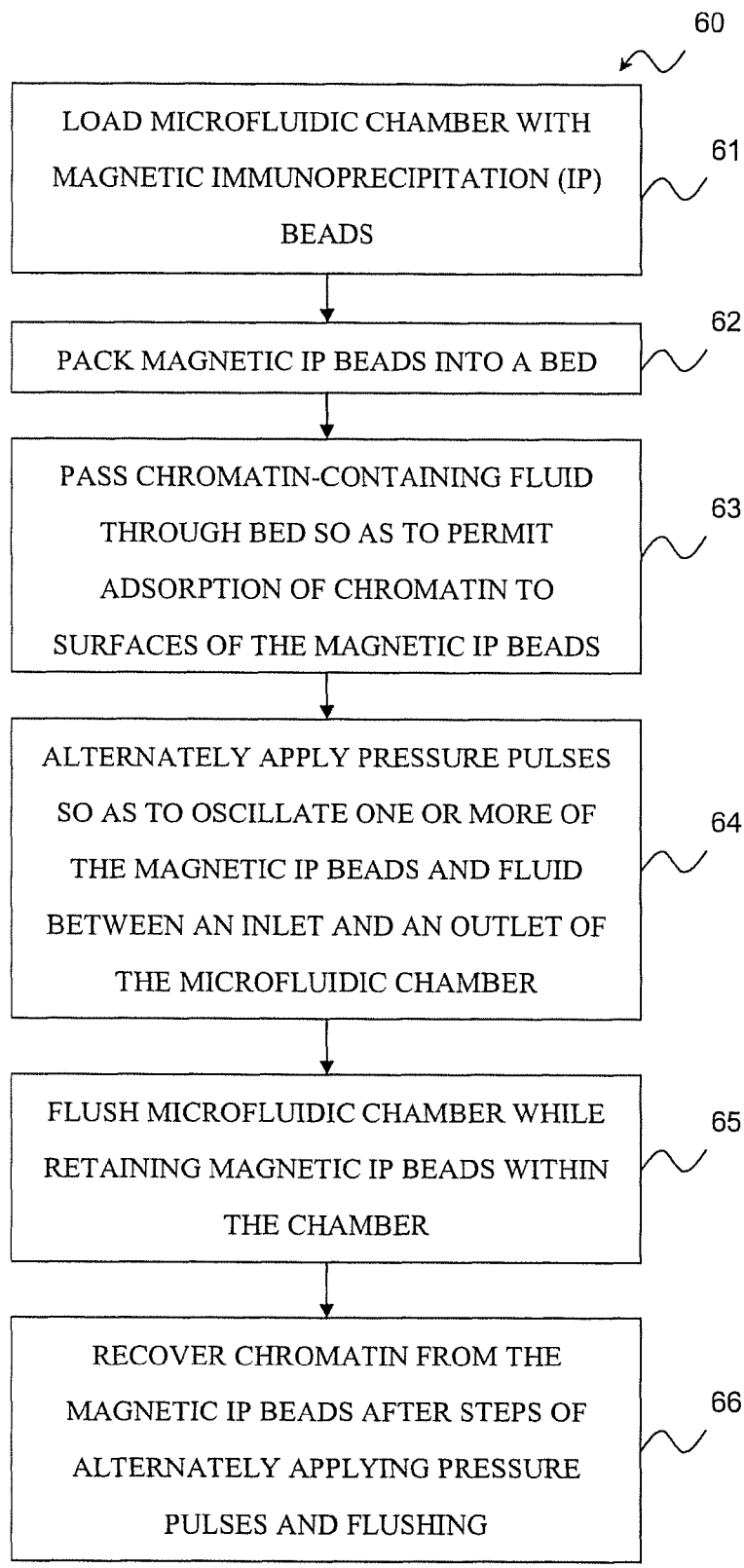
FIG. 6 shows a flowchart of an exemplary ChIP procedure.

Microfluidic ChIP was then performed in accordance with the description and details provided above. FIG. 6 shows a brief flowchart summarizing an exemplary microfluidic ChIP procedure 60. At block 61, a microfluidic chamber 6 is loaded with a plurality of magnetic immunoprecipitation (IP) beads 7 (see FIG. 2A). At block 62, the plurality of magnetic IP beads 7 are packed into a bed (see FIG. 2A). At block 63, chromatin-containing fluid is passed through the bed so as to permit adsorption of chromatin to surfaces of the magnetic IP beads (see FIG. 2B). At block 64, alternating pressure pulses are applied so as to oscillate one or more of the plurality of magnetic IP beads 7 and a fluid between an inlet and an outlet of the microfluidic chamber (see FIG. 3A-3D). The fluid may be a washing buffer, a chromatin-containing fluid, or some other fluid or solution or buffer suitable for washing the beads. It is worth noting that a washing buffer as used in the present example may still be referred to as a chromatin-containing fluid or solution owing to the fact that the buffer suspends chromatin fragments which are not adsorbed to the IP beads 7. While it is preferable to introduce a fresh washing buffer after passing the initial chromatin-containing solution 9 through the bed of IP beads 7, the IP beads 7 may alternatively be washed in the original solution 9. However, this shortcut may have drawbacks such as a reduction in the relative fold enrichment of the recovered ChIP DNA. At block 65, the microfluidic chamber 6 is flushed to remove debris and unbound chromatin fragments while the magnetic IP beads 7 are retained in the microfluidic chamber 6 (see FIG. 4A). Blocks 64 and 65, that is to say the washing and flushing steps, may be repeated for a plurality of iterations with new fluid for washing being introduced into the microfluidic chamber 6 with each flushing. At block 66, after completing the one or more oscillating washing steps and flushing steps, the magnetic IP beads 7 are collected (see FIG. 4B) and the bound chromatin recovered therefrom for completion of a full ChIP assay.

After the microfluidic ChIP process 60, for qPCR analysis, ChIP DNA was extracted from the IP beads 7 using the Chelex (Bio-Rad) resin method described previously[20]. For ChIP-seq assays and next-generation sequencing library preparation, IPure kit (Diagenode, Denville, N.J.) was used to extract and purify the ChIP DNA because the Chelex method interferes with the DNA library preparation step. The purified DNA was used directly in qPCR or in DNA sequencing library preparation.

The level of histone modification at target genomic sites was quantitatively measured by real-time PCR using iQ SYBR Green Supermix (Bio-Rad, Hercules, Calif., USA) on an CFX96 real-time PCR machine with C1000Tm thermal cycler base (BioRad, Hercules, Calif., USA). The ChIP-qPCR result was measured using Percent Input Method. With this method, signals obtained from ChIP samples were divided by signals obtained from the input sample (after normalization based on the amounts of various samples). The equation to calculate the percent input is as following:

$$\text{Percent input} = 100 \times \qquad (1)$$

$$2^{\wedge}\left(\left(Ct_{input} - \log\left(\frac{\text{(Sample Volume of Input + Sample Volume of ChIP)}}{\text{(Sample Volume of Input)}}\right)\right)\bigg/\log 2\right) - Ct_{IP}\right)$$

Where $Ct_{input}$ is the Ct value of input DNA, $Ct_{IP}$ is the Ct value of ChIP DNA. PCR primers used to detect positive and negative loci were designed based on the ChIP-Seq data on the histone modifications in GM 12878 cells in the published ENCODE database, and their sequences are provided in Table 1.

Figure 7A:
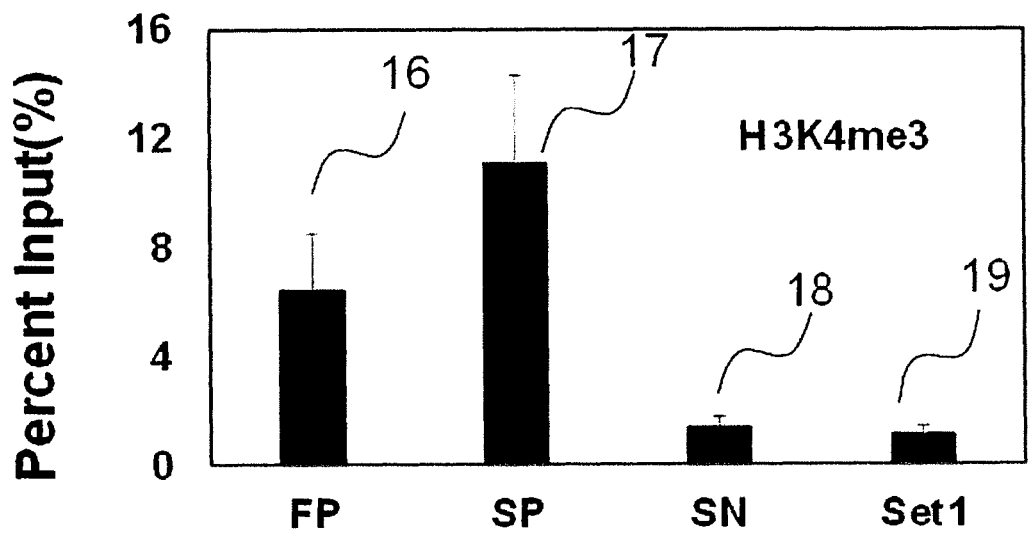
FIG. 7A-7B shows two (2) bar graphs comparing percent input data for positive and negative loci related to two different histone H3 modifications.
Figure 7B:
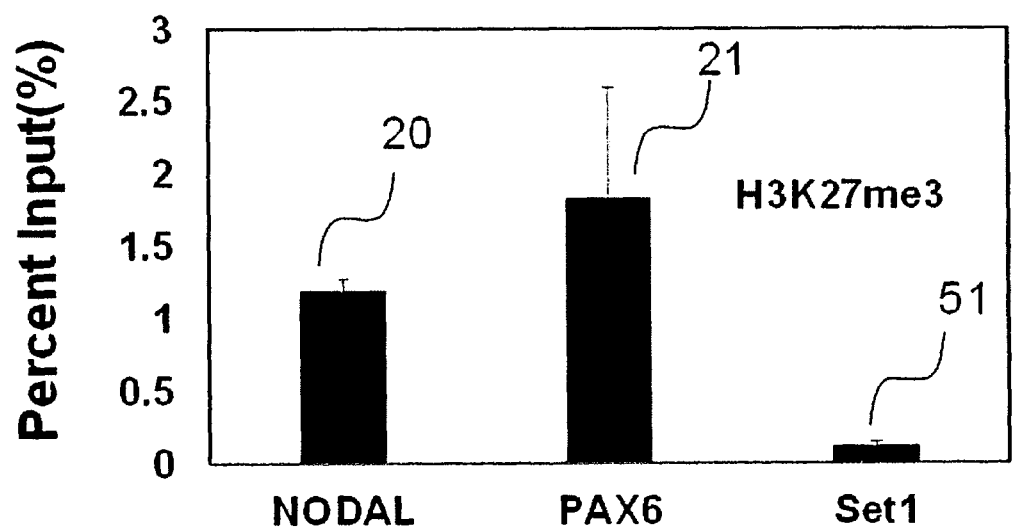

FIGS. 7A and 7B confirm that the percent inputs are substantially higher on known positive loci than on known negative ones. This indicates that the ChIP DNA produced by the microfluidic ChIP system (e.g., FIG. 1A) reliably reveals the histone modifications along various genomic loci.

TABLE 1

Sequences of the primers used in qPCR to evaluate histone modification enrichment at various loci in GM 12878 cells (Primers for human negative Set1 were purchased from Active Motif, Carlsbad, CA and the sequences are unknown).

For H3K4me3

| | | |
|---|---|---|
| First positive (FP) | F | AGG ATA ATC AGC CCC TGA ATA (SEQ ID NO: 1) |
| | R | TCC ATC AGT CAG TCC GCA GT (SEQ ID NO: 2) |
| Second positive (SP) | F | CAG CCA CCC ACC TAG GAA (SEQ ID NO: 3) |
| | R | TCC TAT GGC TCC CCA GGT (SEQ ID NO: 4) |
| Second negative (SN) | F | TCA TCT GCA AAT GGG GAC AA (SEQ ID NO: 5) |
| | R | AGG ACA CCC CCT CTC AAC AC (SEQ ID NO: 6) |
| Human Negative Set1 | F | ATGGTTGCCACTGGGGATCT (SEQ ID NO: 7) |
| (Set1) | R | TGCCAAAGCCTAGGGGAAGA (SEQ ID NO: 8) |

For H3K27me3

| | | |
|---|---|---|
| NODAL | F | CAG CAC CTC CAG CCC TTA T (SEQ ID NO: 9) |
| | R | TCC CCA GAG GGA GGA AAG (SEQ ID NO: 10) |
| PAX6 | F | CTC GGC CTT GAT CTT CTC C (SEQ ID NO: 11) |
| | R | TCT GGC TTT CTT CGC TTT TC (SEQ ID NO: 12) |
| TP | F | CGT CTT CGT ATG CCA TCA AC (SEQ ID NO: 13) |
| | R | GTT GAA CAC GGG TCA GTC G (SEQ ID NO: 14) |

All PCR assays were performed using the following thermal cycling profile: 95° C. for 10 min followed by 40 cycles of (95° C. for 15 s, 56° C. for 30 s, 72° C. for 30 s). Primer concentrations were 400 nM. All the primers were ordered from Integrated DNA Technologies (Coralville, Iowa, USA). The quality and specificity of all primer pairs were confirmed by performing melting curve analysis.

Figure 8A:
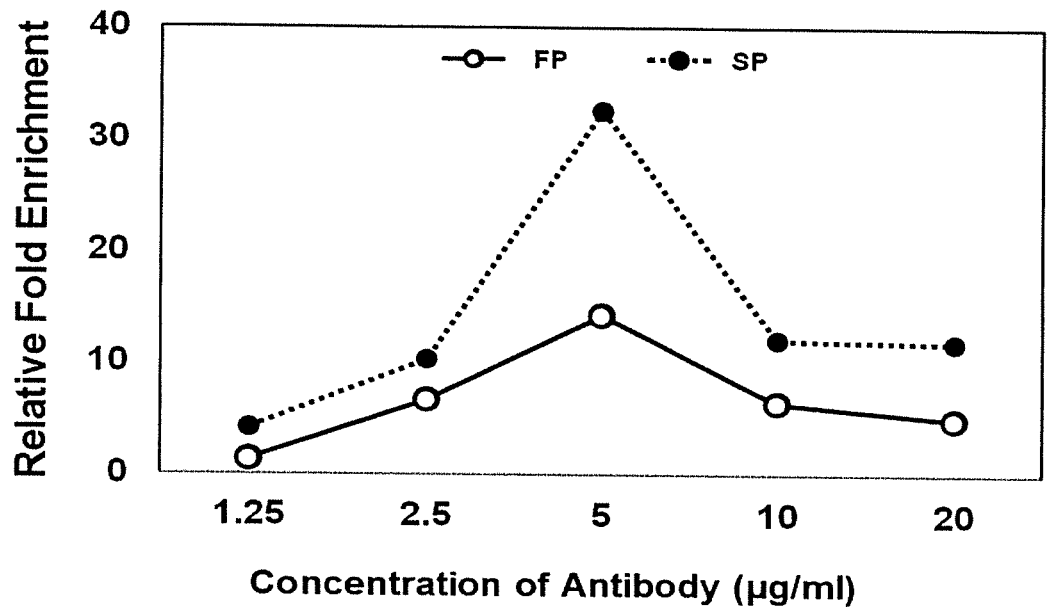
FIG. 8A-8D show relative fold enrichment (i.e. the ratio between the percent input at a positive locus and that at the negative locus Set 1) data under various experimental conditions (i.e. the antibody concentration for coating IP beads and the volumetric fraction of the IP beads in the microfluidic chamber) for microfluidic ChIP. 10000 cells were used in each sample to examine both H3K4me3 (FIGS. 8A and 8B) and H3K27me3 (FIGS. 8C and 8D). Experiments in FIGS. 8A and 8C were conducted using a volumetric fraction of 22.4% for the IP beads. The antibody concentration of 5 μg/ml and 10 μg/ml were used in FIGS. 8B and 8D, respectively.
Figure 8B:
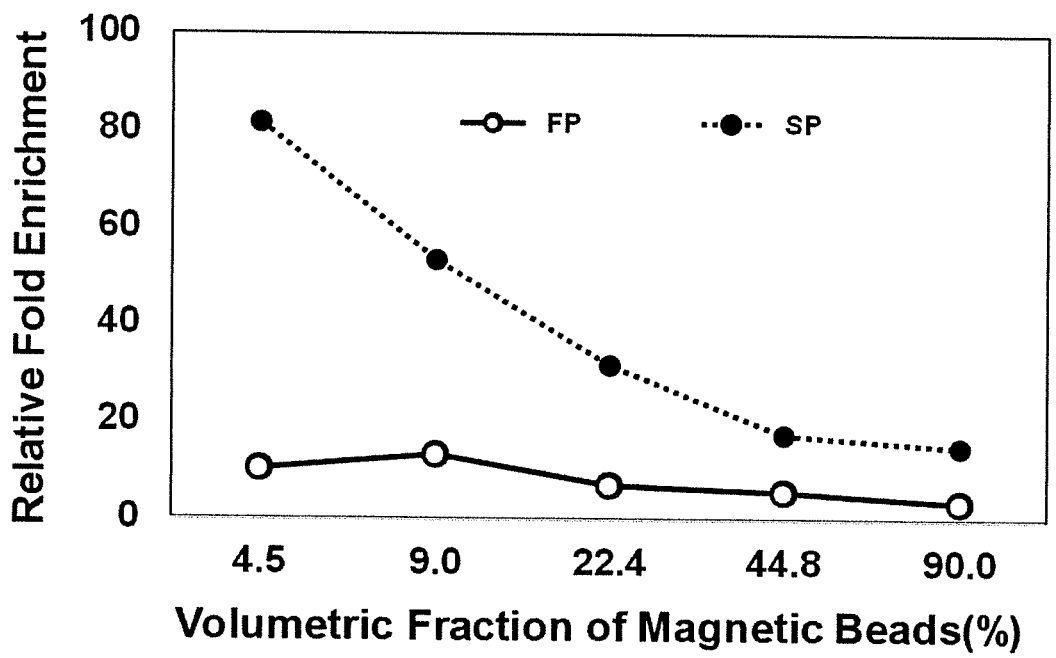
Figure 8C:
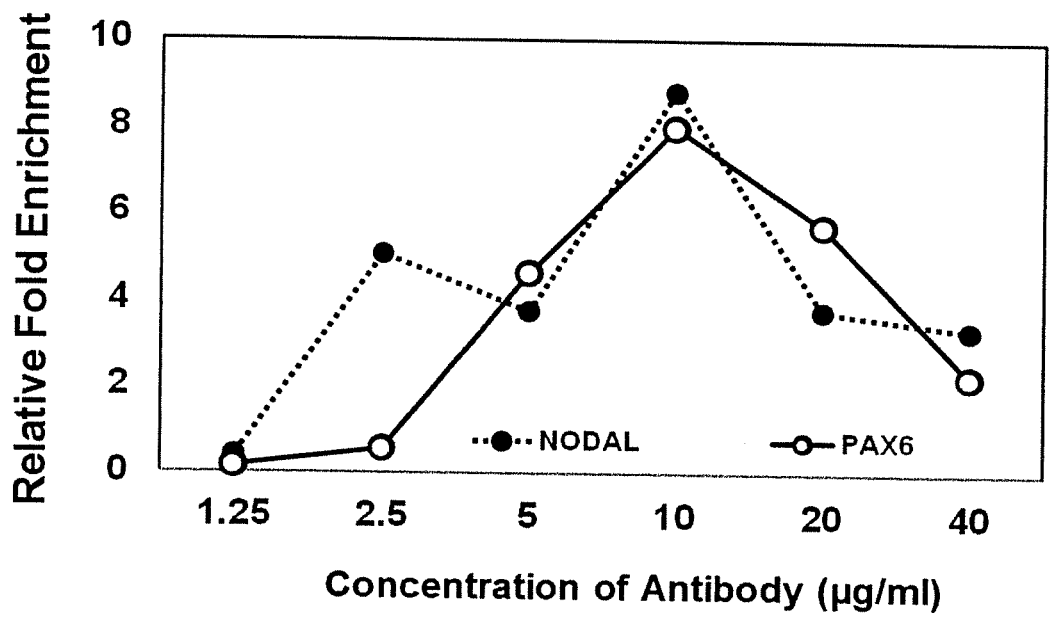
Figure 8D:
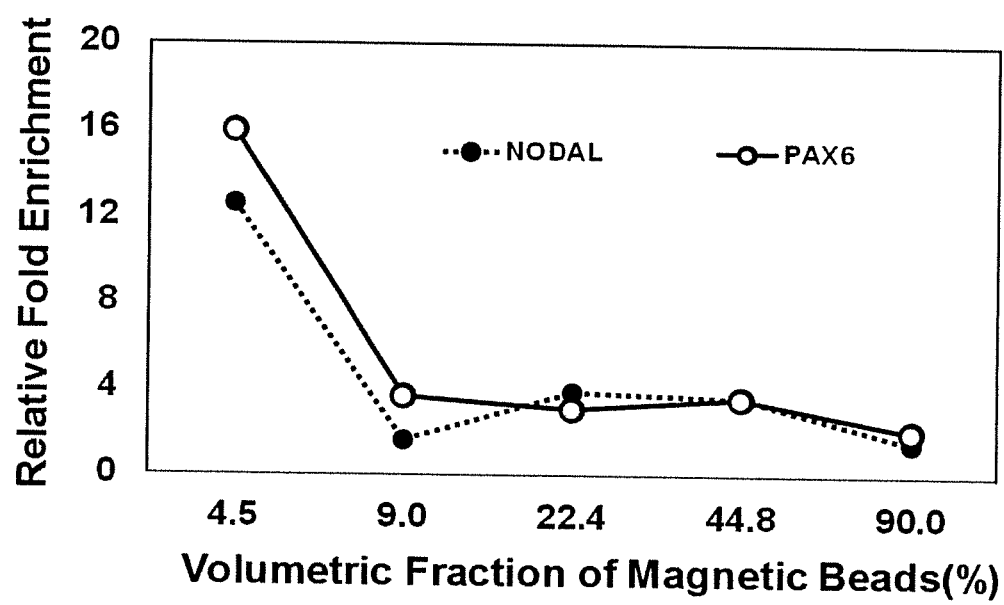

Resulting data demonstrate the effectiveness of a microfluidic ChIP system and procedures according to the teachings herein for high-efficiency extraction of high-quality ChIP DNA that can be used for qPCR analysis, DNA library preparation, and next-generation sequencing. As shown in FIGS. 7A and 7B, aforementioned qPCR was used to quantify the percent input of ChIP DNA extracted from 10000 GM 12878 cells at known positive and negative loci for both H3K4me3 (FIG. 7A) and H3K27me3 (FIG. 7B). FIG. 7A shows results for ChIP using anti-H3K4me3 (antibody against trimethyl-Histone H3 (Lys4)) coated IP beads. FP 16 and SP 17 are two known positive sites for H3K4me3, while SN 18 and Set1 19 are two negative regions for H3K4me3. FIG. 7B shows tests using anti-H3K27me3 (antibody against trimethyl-Histone H3 (Lys27)). NODAL 20 and PAX6 21 are two positive sites for H3K27me3, while Set1 51 is negative for H3K27me3. Microfluidic ChIP was performed starting with sonicated (i.e. fragmented) chromatin extracted from 10,000 GM 12878 cells. The percent input was calculated according to Eqn. 1 above. Error bars were generated by three ChIP-qPCR replicates. The results in In addition, we optimized our protocols by examining the relative fold enrichment under various experimental conditions (i.e. bead-coating condition (the antibody concentration) and the amount of magnetic IP beads during microfluidic ChIP) in FIG. 8A-8D (with 10000 cells) and FIG. 9A-9D (with 1000 and 3000 cells). The relative fold enrichment, which was generated by normalizing the percent input at positive loci against that at the negative control region on chromosome 12 (sea), reveals the quality of the ChIP DNA. We varied the antibody coating condition for the IP beads by changing the antibody concentration in the coating solution (FIGS. 8A and 8C). 4 µl Dynal bead suspension (corresponding to 22.4% in the volumetric fraction which will be discussed below in relation to FIGS. 8B and 8D) was added to 100 µl PBS buffer that contained either anti-H3K4me3 (FIG. 8A) or anti-H3K27me3 (FIG. 8C) of a certain concentration during the antibody conjugation to the bead surface. We show that the relative fold enrichment was the highest for both FP and SP when the antibody (anti-H3K4me3) concentration was 5 µg/ml (FIG. 7A) and it was the maximum for both NODAL and PAX6 when the antibody (anti-H3K27me3) concentration was 10 µg/ml (FIG. 7C). After optimizing the coating condition, we further optimized the amount of IP beads used in microfluidic ChIP while the coating was done at the optimal antibody concentration. We varied the volumetric fraction of beads (i.e. the volume of the beads divided by the volume of the microfluidic ChIP chamber which was 800 nl) in FIG. 8B (H3K4me3) and 8D (H3K27me3). In general, higher volumetric fraction of beads led to lower relative fold enrichment. This suggests that a balance must be struck between the amount of ChIP DNA recovered and the quality of what is recovered. While higher volumetric fractions of IP beads generally gives more adsorption and thus more recovered chromatin, it may also have the drawback of reducing the relative fold enrichment.

Figure 9A:
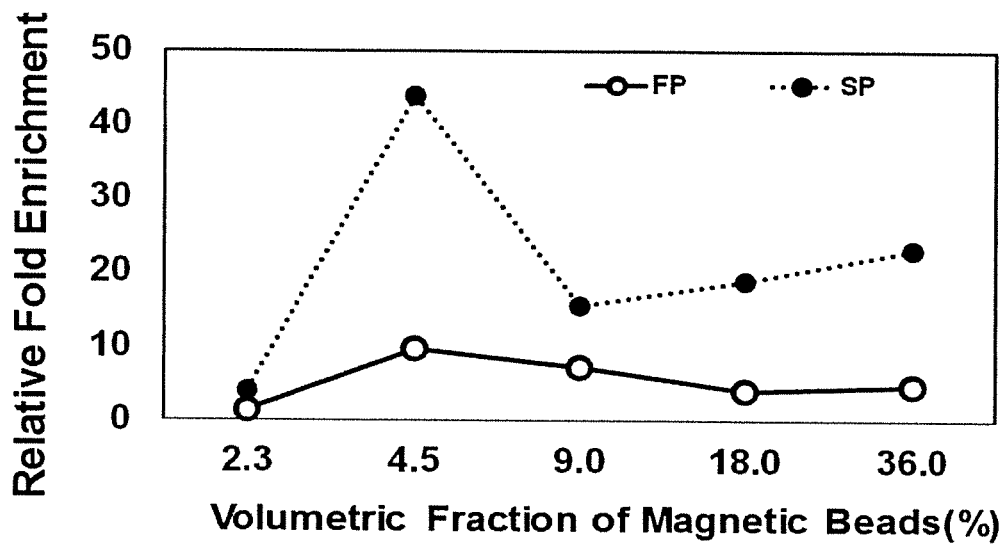
FIG. 9A-9D show relative fold enrichment (i.e. the ratio between the percent input at a positive locus and that at the negative locus Set 1) data under various experimental conditions (i.e. the antibody concentration for coating IP beads and the volumetric fraction of the IP beads in the microfluidic chamber) for microfluidic ChIP with 3000 and 1000 cells. This figure shows optimization of H3K4me3 ChIP with only 3000 cells (FIGS. 9A and 9B) and 1000 cells (FIGS. 9C and 9D). Experiments in FIGS. 9A and 9C were conducted using an antibody concentration of 5 μg/ml. A volumetric fraction of 18% for the IP beads was used in FIGS. 9B and 9D.
Figure 9B:
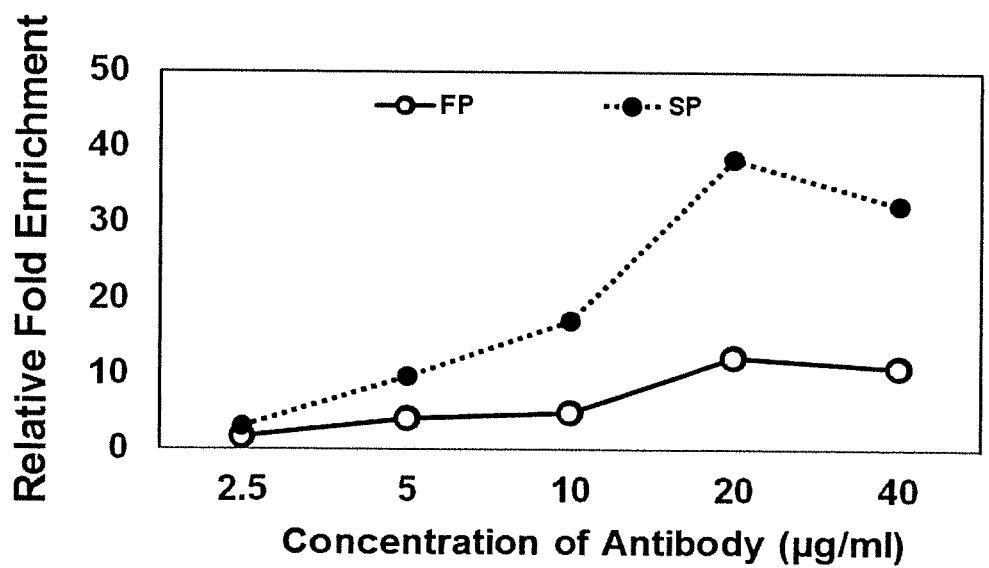
Figure 9C:
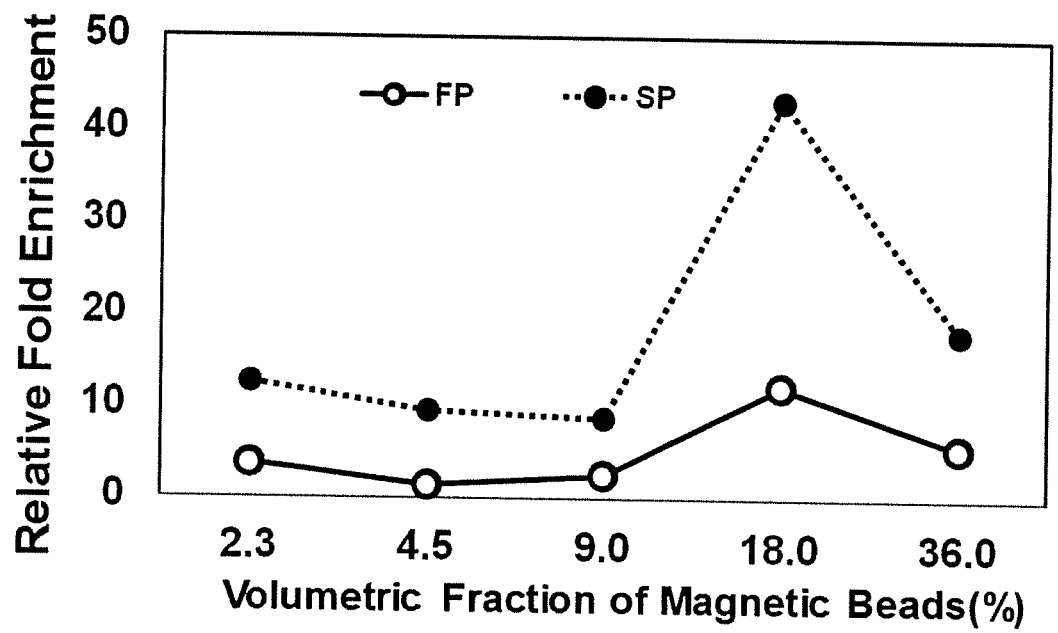
Figure 9D:
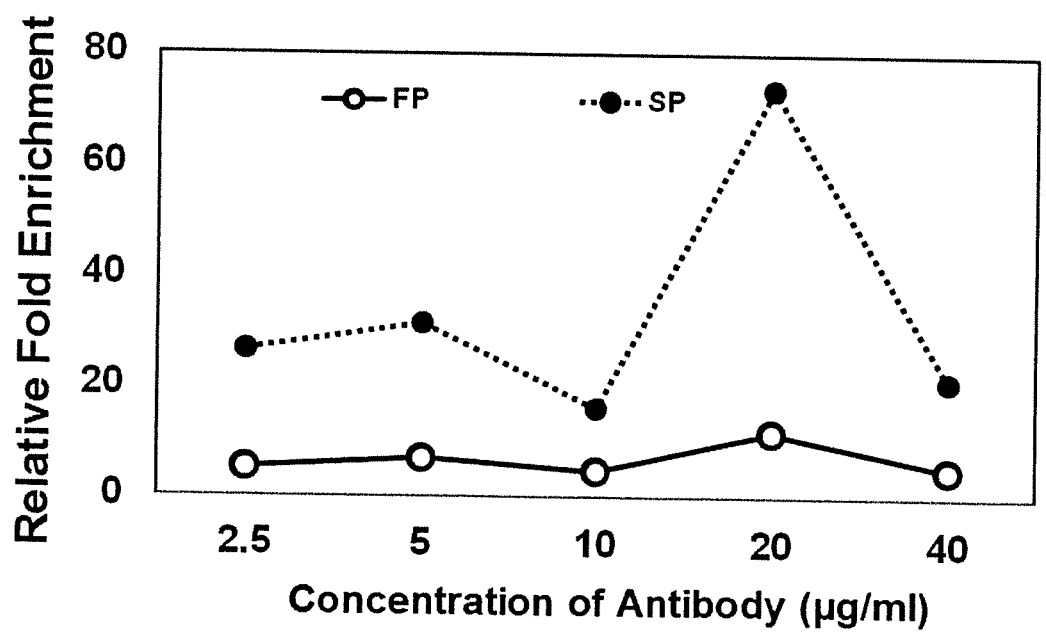

Similarly, the experimental conditions of microfluidic ChIP (targeting H3K4me3) have also been optimized using 3000 cells (FIGS. 9A and 9B) and 1000 cells (FIGS. 9C and 9D). FIGS. 9A and 9C show the results on the optimization of the volumetric fraction of beads. FIGS. 9B and 9D show the optimization of the coating antibody concentration.

Figure 10:
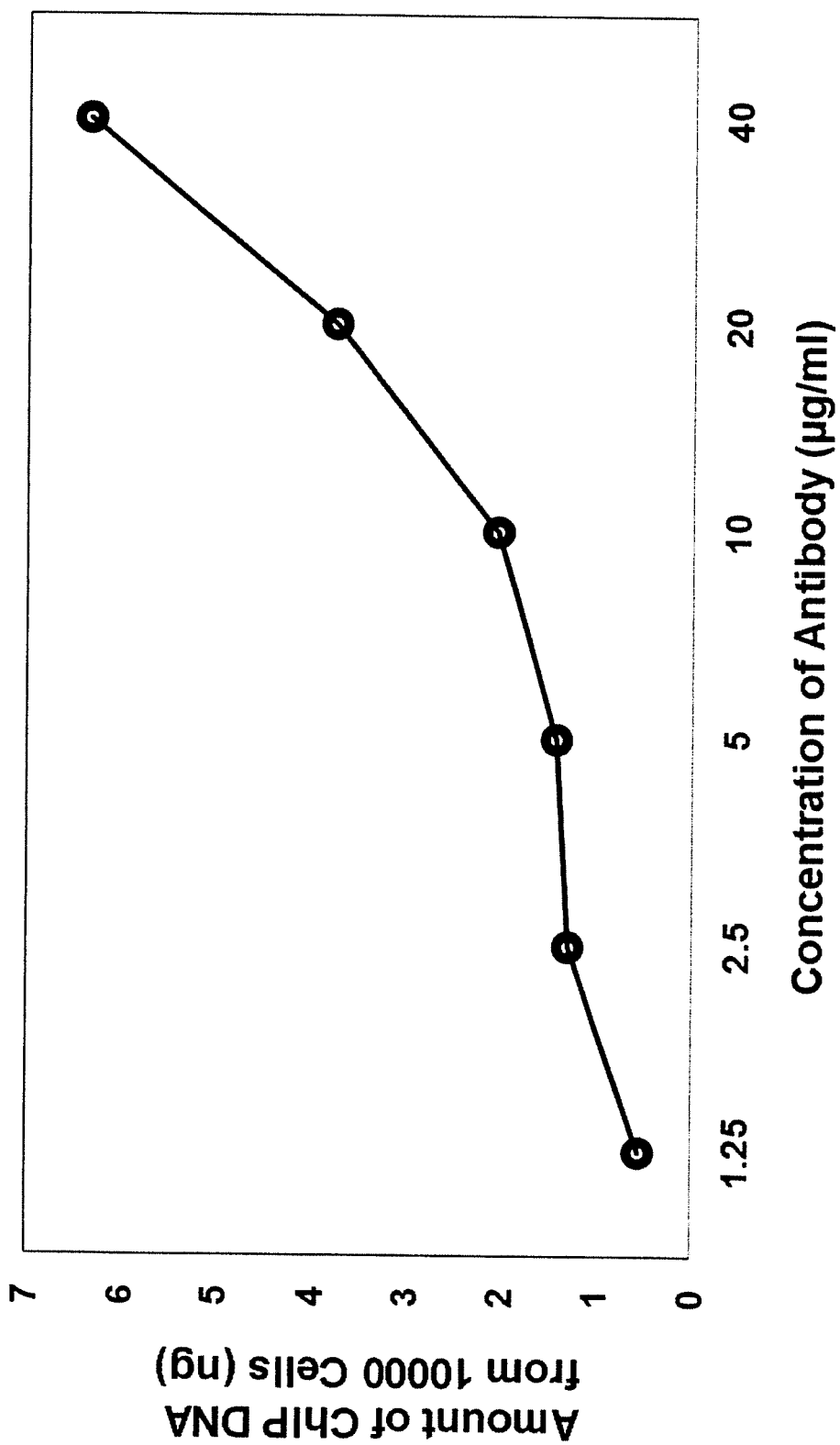
FIG. 10 shows the amount of ChIP DNA extracted from 10000 cells under various antibody (anti H3K4me3) concentrations (during coating of IP beads).

FIG. 10 shows how the yield of ChIP DNA from 10000 cells varied with the antibody concentration (for examining H3K4me3). The DNA amount was quantified using Qubit (Life Technologies, Carlsbad, Calif.). A volumetric fraction of 22.4% was used for the beads in all tests. FIG. 10 reveals that higher antibody concentration during bead coating led to increase in the DNA yield. We were able to obtain 2-3 ng ChIP DNA with a medium antibody concentration of ~10 µg/ml. This amount is roughly 100 fold larger than that in the previous report (10~50 pg)[25].

Figures 11A, 11B:
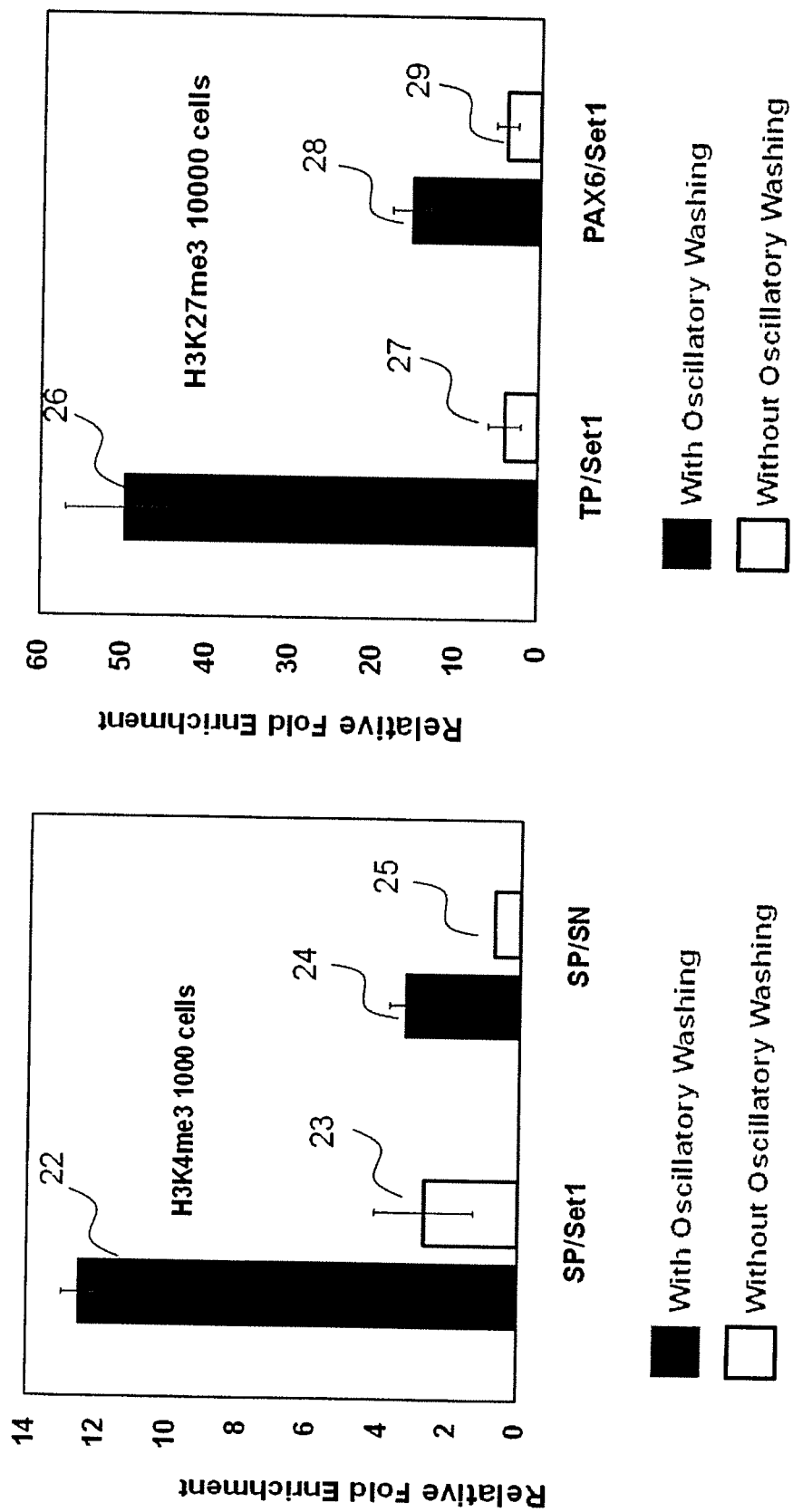
FIGS. 11A and 11B show the relative fold enrichment with and without microfluidic oscillatory washing.

FIG. 11A-11B shows that the oscillatory washing was critical for obtaining high quality ChIP DNA. We compare the relative fold enrichment of obtained DNA between groups with "on-chip oscillatory washing" and groups without oscillating washing. Microfluidic ChIP tests with different cell numbers (FIG. 11A:1000 cells, FIG. 11B:10000 cells) were performed. In FIG. 11A, the relative fold enrichment (22-25) was calculated by normalizing the percent input of H3K4me3 positive site SP against either of two K4 negative sites: Set1 or SN. In FIG. 11B, the two positive sites for H3K27me3, TP and PAX6, was normalized against the negative site Set1 (26-29). In both cases, groups with oscillatory washing yield significantly higher enrichment folds than the control groups without the washing.

Figure 12:
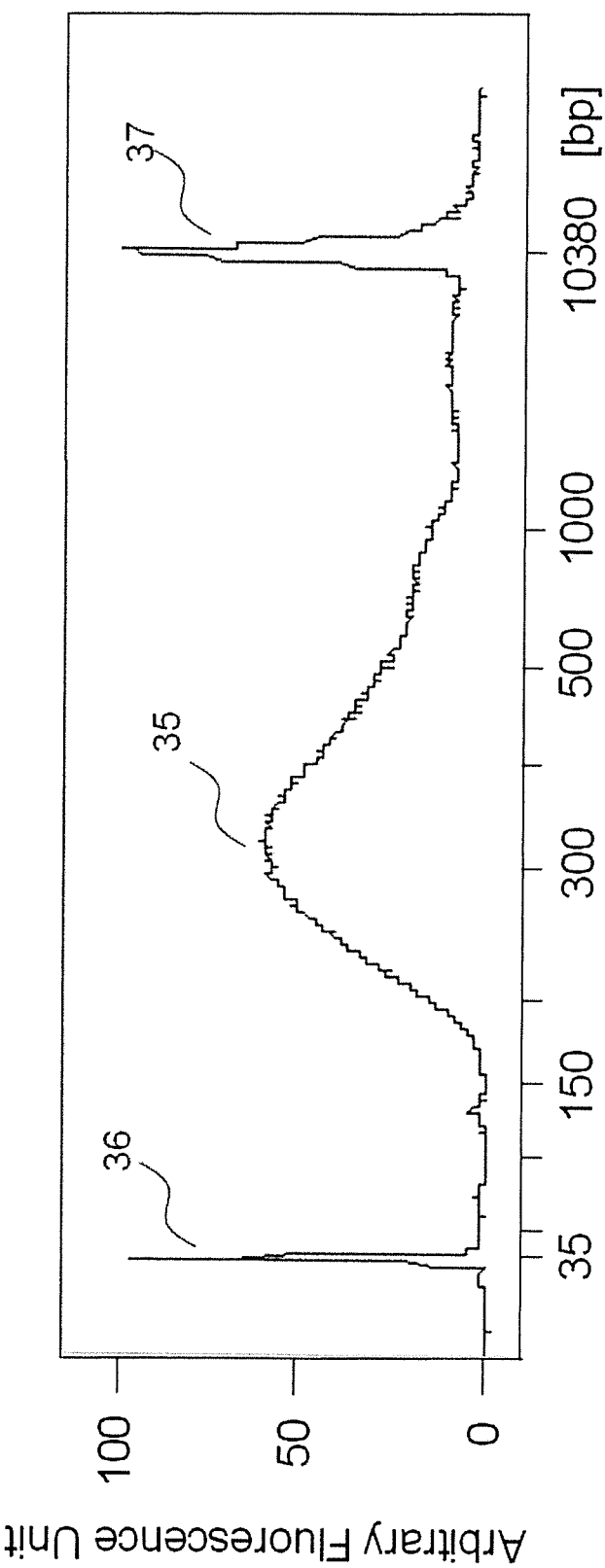
FIG. 12 shows the fragment size of the pooled DNA library prepared from ChIP DNA extracted from 10000 cells using the microfluidic device of an exemplary embodiment. The data were taken using a bioanalyzer (Agilent, Santa Clara, Calif., USA).
Figure 13A:
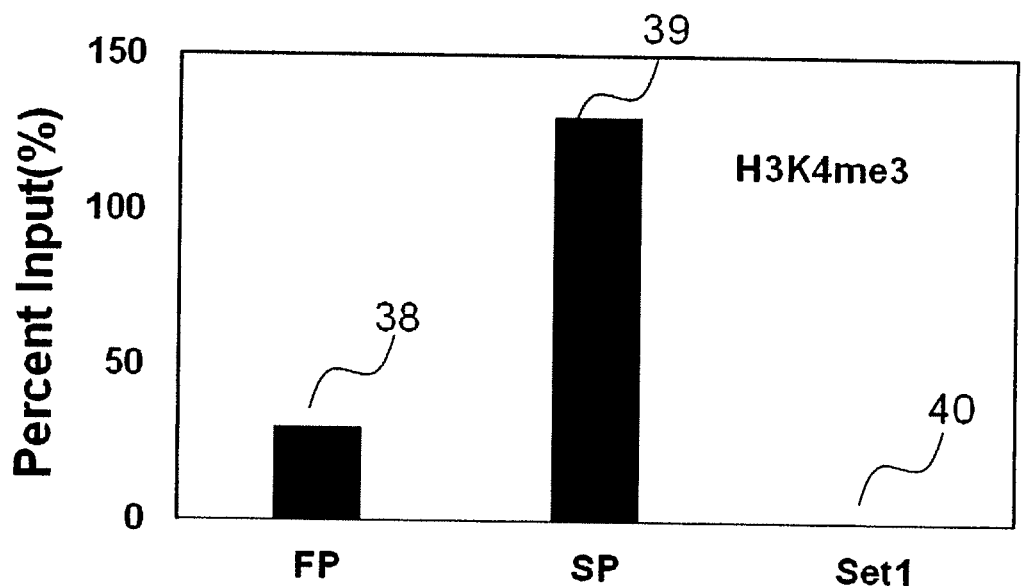
FIGS. 13A and 13B are two (2) bar graphs showing the percent input data taken using the DNA library prepared with ChIP DNA extracted from 10000 cells. The DNA library was diluted by 10000 times before qPCR testing.
Figure 13B:
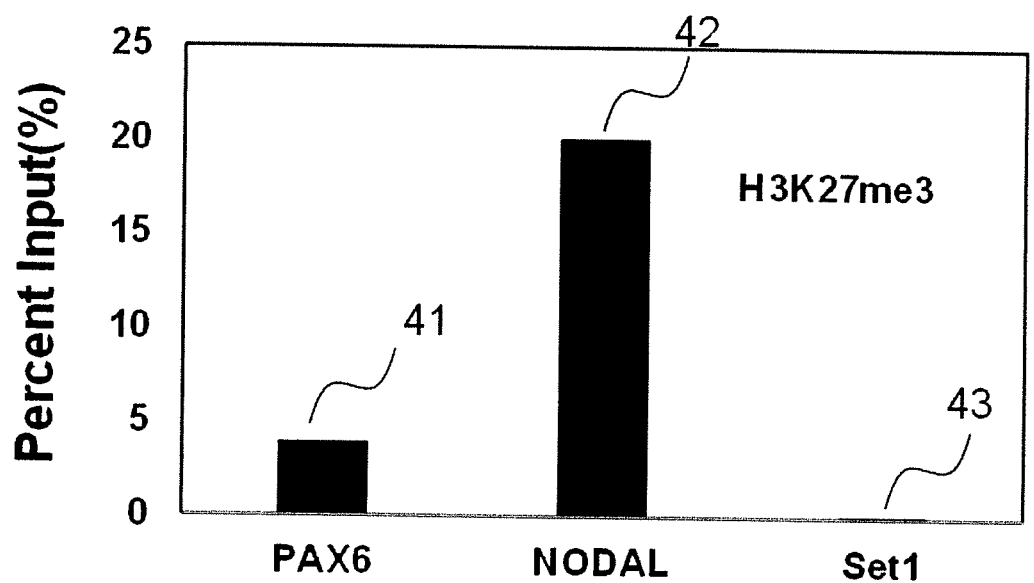

We also prepared DNA library for next-generation sequencing successfully from ChIP DNA produced by the present system shown in FIG. 1A using ThruPLEX-FD kit (Rubicon Genomics, Ann Arbor, Mich., USA). This indicates that ChIP DNA produced by our system can be readily used for ChIP-seq purpose. The sizing and quantification data of the pooled library (before sequencing) is shown by 35 of FIG. 12. Two peaks, which correspond to markers of 35 bp 36 and 10380 bp 37, are also shown in FIG. 12. The average fragment size of the pooled library was around 300 bp, which is ideal for next generation sequencing with Illumina sequencers. After the DNA library preparation, we conducted enrichment tests of the diluted library samples. The results, as shown in FIG. 13A-13B, confirm that the DNA library prepared from ChIP DNA maintained the original enrichment patterns for the positive and negative loci.

Figure 14:
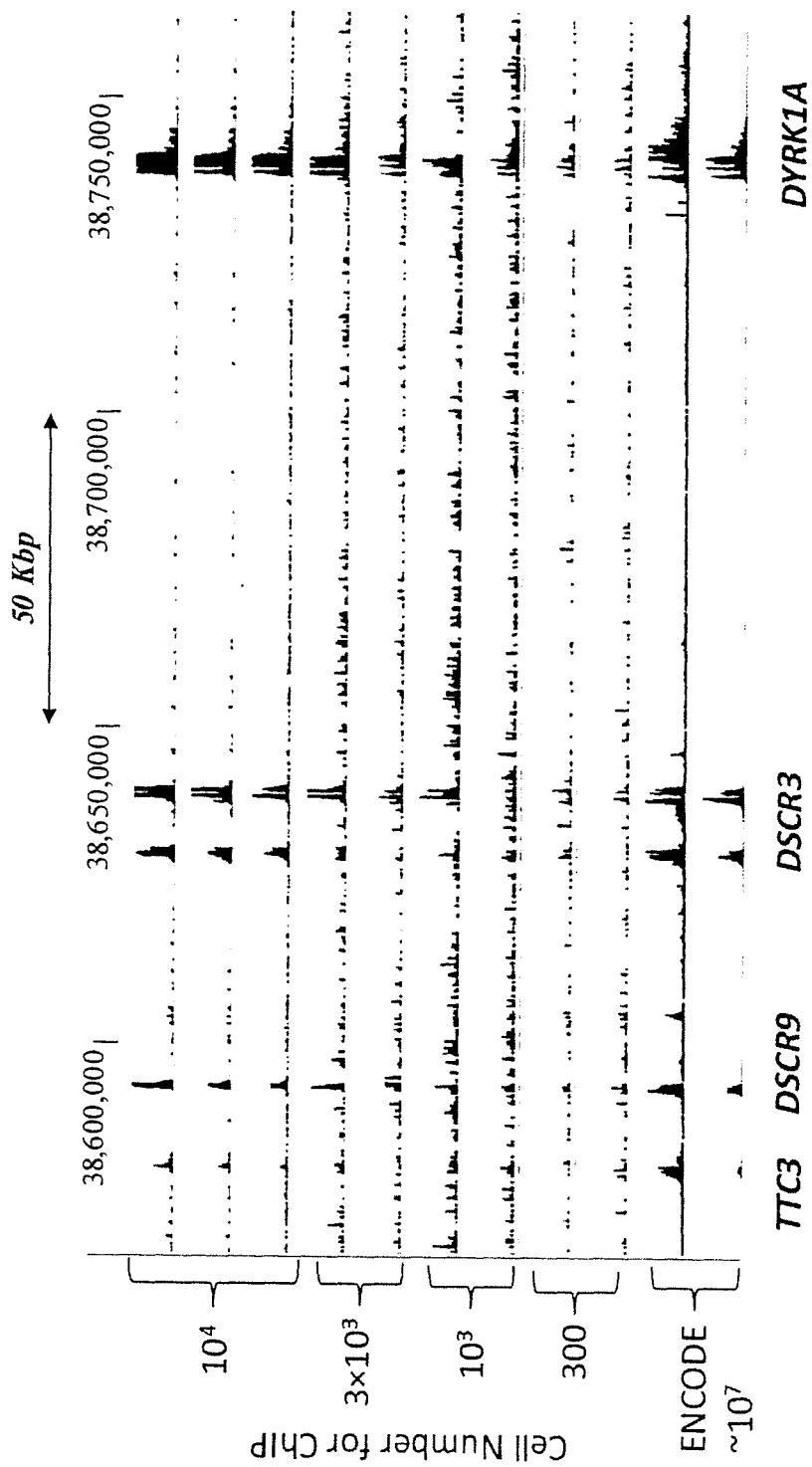
FIG. 14 shows normalized H3K4me3 profiles of peaks found in a 200-kb region (genes are indicated below) in the genome obtained with a microfluidic ChIP-seq using various numbers of cells (10,000 to 300 cells). (Top) H3K4me3 profiles obtained with microfluidic ChIP-seq using 10,000 to 300 cells. (Below) ENCODE data from the literature: H3K4me3 profiles obtained using conventional ChIP using 10-20 million cells.

We conducted whole-genome sequencing of the ChIP DNA (ChIP-seq) produced by our technology at Virginia Bioinformatics Institute using Illumina HiSeq 2500. As shown in FIG. 14, microfluidic ChIP-seq reveals the histone modification profile of H3K4me3 under a series of GM12878 cell sample sizes (300~10000 cells). The detected peaks, which indicated histone modification H3k4me3 in the genome, appear mostly at the promoter regions of specific genes. There was good agreement between our data and the published ENCODE data (the Broad Inst. Data and the UW data) which were taken by conventional ChIP-seq using 10-20 million of cells. In Table 2, we compare the whole-genome overlapping rate of our microfluidic ChIP-seq data (3000 cells and 10000 cells, H3k4me3) with ENCODE data. The high overlapping rate (>50%) indicates the high quality our ChIP-seq data.

TABLE 2

Overlapping with ENCODE data

| Sample | # Identified peaks | # Peaks overlapped with Broad Inst. Data | # Peaks overlapped with UW data |
|---|---|---|---|
| H3K4me3, 3000 cells | 20,174 | 12,255 (60.8%) | 12,061 (59.8%) |
| H3K4me3, 10000 cells, Rep 1 | 30,982 | 18,030 (58.2%) | 17,393 (56.1%) |
| H3K4me3, 10000 cells, Rep 2 | 26,889 | 16,500 (61.4%) | 16,176 (60.2%) |

REFERENCES

1. E. L. Greer and Y. Shi, *Nat Rev Genet*, 2012, 13, 343-357.
2. K. D. Robertson, *Nat Rev Genet*, 2005, 6, 597-610.
3. C. E. Massie and I. G. Mills, *EMBO Rep*, 2008, 9, 337-343.
4. H. J. Oh, J. Y. Park, S. E. Park, B. Y. Lee, J. S. Park, S.-K. Kim, T. J. Yoon and S.-H. Lee, *Analytical chemistry*, 2009, 81, 2832-2839.
5. P. J. Farnham, *Nat Rev Genet*, 2009, 10, 605-616.
6. P. Collas, *Mol Biotechnol*, 2010, 45, 87-100.
7. A. J. Bannister, P. Zegerman, J. F. Partridge, E. A. Miska, J. O. Thomas, R. C. Allshire and T. Kouzarides, *Nature*, 2001, 410, 120-124.
8. R. Cao, L. Wang, H. Wang, L. Xia, H. Erdjument-Bromage, P. Tempst, R. S. Jones and Y. Zhang, *Science*, 2002, 298, 1039-1043.
9. H. Santos-Rosa, R. Schneider, A. J. Bannister, J. Sherriff, B. E. Bernstein, N. C. T. Emre, S. L. Schreiber, J. Mellor and T. Kouzarides, *Nature*, 2002, 419, 407-411.
10. A. A. Bhinge, J. Kim, G. M. Euskirchen, M. Snyder and V. R. Iyer, *Genome Res*, 2007, 17, 910-916.
11. A. Valouev, D. S. Johnson, A. Sundquist, C. Medina, E. Anton, S. Batzoglou, R. M. Myers and A. Sidow, *Nat Methods*, 2008, 5, 829-834.
12. P. V. Kharchenko, M. Y. Tolstorukov and P. J. Park, *Nat Biotechnol*, 2008, 26, 1351-1359.
13. L. P. O'Neill and B. M. Turner, *Methods Enzymol*, 1996, 274, 189-197.
14. V. A. Spencer, J. M. Sun, L. Li and J. R. Davie, *Methods*, 2003, 31, 67-75.
15. L. P. O'Neill, M. D. VerMilyea and B. M. Turner, *Nat Genet*, 2006, 38, 835-841.
16. J. D. Nelson, O. Denisenko and K. Bomsztyk, *Nat Protoc*, 2006, 1, 179-185.
17. L. G. Acevedo, A. L. Iniguez, H. L. Holster, X. Zhang, R. Green and P. J. Farnham, *Biotechniques*, 2007, 43, 791-797.
18. J. L. Attema, P. Papathanasiou, E. C. Forsberg, J. Xu, S. T. Smale and I. L. Weissman, *Proc Natl Acad Sci USA*, 2007, 104, 12371-12376.
19. J. A. Dahl and P. Collas, *Stem Cells*, 2007, 25, 1037-1046.
20. J. A. Dahl and P. Collas, *Nature protocols*, 2008, 3, 1032-1045.
21. A. R. Wu, J. B. Hiatt, R. Lu, J. L. Attema, N. A. Lobo, I. L. Weissman, M. F. Clarke and S. R. Quake, *Lab on a Chip*, 2009, 9, 1365-1370.

22. M. Adli, J. Zhu and B. E. Bernstein, *Nat Methods,* 2010, 7, 615-618.
23. P. Shankaranarayanan, M. A. Mendoza-Parra, M. Walia, L. Wang, N. Li, L. M. Trindade and H. Gronemeyer, *Nat Methods,* 2011, 8, 565-567.
24. A. Goren, F. Ozsolak, N. Shoresh, M. Ku, M. Adli, C. Hart, M. Gymrek, O. Zuk, A. Regev, P. M. Milos and B. E. Bernstein, *Nat Methods,* 2010, 7, 47-49.
25. M. Adli and B. E. Bernstein, *Nature Protocols,* 2011, 6, 1656-1668.
26. T. D. Harris, P. R. Buzby, H. Babcock, E. Beer, J. Bowers, I. Braslaysky, M. Causey, J. Colonell, J. Dimeo, J. W. Efcavitch, E. Giladi, J. Gill, J. Healy, M. Jarosz, D. Lapen, K. Moulton, S. R. Quake, K. Steinmann, E. Thayer, A. Tyurina, R. Ward, H. Weiss and Z. Xie, *Science,* 2008, 320, 106-109.
27. P. J. Park, *Nature Reviews Genetics,* 2009, 10, 669-680.
28. S. P. Chellappan, *Chromatin protocols,* Humana Press, New York, N.Y., 2009.
29. M. A. Unger, H. P. Chou, T. Thorsen, A. Scherer and S. R. Quake, *Science,* 2000, 288, 113-116.
30. T. Geng, N. Bao, M. D. Litt, T. G. Glaros, L. Li and C. Lu, *Lab Chip,* 2011, 11, 2842-2848.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

What is claimed is:

1. A microfluidic chromatin immunoprecipitation system, comprising:
    at least one microfluidic chamber having an inlet and an outlet and sized to accommodate a plurality of magnetic immunoprecipitation (IP) beads and a chromatin-containing fluid;
    one or more solenoid valves in fluid communication with said inlet and said outlet of said at least one microfluidic chamber; and
    a controller configured to actuate said one or more solenoid valves to cyclically alternate pressure pulses at a selected frequency so as to oscillate one or more of said plurality of magnetic IP beads and a fluid between said inlet and said outlet of said at least one microfluidic chamber.

2. The microfluidic chromatin immunoprecipitation system of claim 1, wherein said at least one microfluidic chamber is formed on a microfluidic chip.

3. The microfluidic chromatin immunoprecipitation system of claim 2, wherein said at least one microfluidic chamber includes a plurality of microfluidic chambers formed on said microfluidic chip.

4. The microfluidic chromatin immunoprecipitation system of claim 2, further comprising one or more on-chip valves allowing a partial closure of at least one of said inlet and said outlet to prevent said plurality of magnetic IP beads from passing and permit said chromatin containing-fluid and said fluid to pass.

5. The microfluidic chromatin immunoprecipitation system of claim 1, wherein said one or more solenoid valves includes a first valve connected to said inlet of said microfluidic chamber and a second valve connected to said outlet of said microfluidic chamber.

6. The microfluidic chromatin immunoprecipitation system of claim 1, wherein said controller is a computer configured for controlling said one or more solenoid valves.

7. A method of microfluidic chromatin immunoprecipitation, comprising steps of:
    loading a microfluidic chamber with a plurality of magnetic immunoprecipitation (IP) beads;
    packing said plurality of magnetic IP beads into a bed;
    passing a chromatin-containing fluid through said bed so as to permit adsorption of chromatin to surfaces of said magnetic IP beads; and
    alternately applying pressure pulses by actuating one or more solenoid valves in fluid communication with an inlet and an outlet of said microfluidic chamber so as to oscillate one or more of said plurality of magnetic IP beads and a fluid between said inlet and said outlet, wherein said pressure pulses cyclically alternate at a selected frequency.

8. The method of claim 7, further comprising a step of flushing said microfluidic chamber after said step of alternately applying pressure pulses, said magnetic IP beads being retained in said microfluidic chamber during said flushing.

9. The method of claim 8, wherein said step of alternately applying pressure pulses and said step of flushing are each repeated for a plurality of iterations.

10. The method of claim 7, further comprising a step of partially closing one or more on-chip valves to allow a partial closure of at least one of said inlet and said outlet so as to prevent said plurality of magnetic IP beads from passing and permit said chromatin-containing fluid and said fluid to pass.

11. The method of claim 7, wherein said loading step fills 15-40% of a volume of said microfluidic chamber with said plurality of magnetic IP beads.

12. An assay which employs a microfluidic chromatin immunoprecipitation process, said assay including steps of:
    loading a microfluidic chamber with a plurality of magnetic immunoprecipitation (IP) beads;
    packing said plurality of magnetic IP beads into a bed;

passing a chromatin-containing fluid through said bed so as to permit adsorption of chromatin to surfaces of said magnetic IP beads;

alternately applying pressure pulses by actuating one or more solenoid valves in fluid communication with an inlet and an outlet of said microfluidic chamber so as to oscillate one or more of said plurality of magnetic IP beads and a fluid between said inlet and said outlet, wherein said pressure pulses cyclically alternate at a selected frequency; and recovering said chromatin from said magnetic IP beads after said step of alternately applying pressure pulses.

13. The assay of claim 12, further comprising a step of flushing said microfluidic chamber after said step of alternately applying pressure pulses, said magnetic IP beads being retained in said microfluidic chamber during said flushing, said step of flushing being performed prior to said step of recovering.

14. The assay of claim 13, wherein said step of alternately applying pressure pulses and said step of flushing are each repeated for a plurality of iterations prior to said step of recovering.

15. The assay of claim 12, further comprising a step of partially closing one or more on-chip valves to allow a partial closure of at least one of said inlet and said outlet so as to prevent said plurality of magnetic IP beads from passing and permit said chromatin-containing fluid and said fluid to pass.

16. The assay of claim 12, wherein said loading step fills 15-40% of a volume of said microfluidic chamber with said plurality of magnetic IP beads.

* * * * *